(12) United States Patent
Wang

(10) Patent No.: US 6,191,266 B1
(45) Date of Patent: Feb. 20, 2001

(54) SUGAR MODIFIED NUCLEOSIDES

(75) Inventor: Guangyi Wang, Irvine, CA (US)

(73) Assignee: ICN Pharmaceuticals, Inc., Costa Mesa, CA (US)

( * ) Notice: Under 35 U.S.C. 154(b), the term of this patent shall be extended for 0 days.

(21) Appl. No.: 08/766,991

(22) Filed: Dec. 16, 1996

Related U.S. Application Data

(60) Division of application No. 08/552,363, filed on Nov. 2, 1995, now Pat. No. 5,712,378, which is a continuation-in-part of application No. 08/333,545, filed on Nov. 2, 1994, now Pat. No. 5,681,940.

(51) Int. Cl.[7] .................. C07H 19/00; C07H 21/02; C07H 21/04; C07H 21/00
(52) U.S. Cl. .................. 536/22.1; 536/23.1; 536/24.3; 536/24.33; 536/25.3
(58) Field of Search ................. 536/22.1, 23.1, 536/24.3, 24.33, 25.3

(56) References Cited

U.S. PATENT DOCUMENTS 5,446,137   8/1995   Maag et al. ................ 536/23.1

FOREIGN PATENT DOCUMENTS

WO 92/20823  * 11/1992  (WO).

OTHER PUBLICATIONS

Rabow L. and Stubbe, J., "Identification of the Alkaline–Labile Product Accompanying Cytosine Release during Bleomycin–Mediated Degradation of d(CGCGCG)", *J. Am. Chem. Soc.* 1986, 108, 7130–7131 (dated 1986).

\* cited by examiner

Primary Examiner—Jezia Riley
(74) Attorney, Agent, or Firm—Fish & Associates, LLP; Robert D. Fish

(57) ABSTRACT

A number of modified nucleosides are disclosed composed of modified sugar moieties which contain substituents at C1 and C4 positions, or branched substituents at C3 and C5 positions of deoxyribose or ribose. Each nucleoside is converted to or properly protected and then converted to the corresponding phosphoramidites. These phosphoramidites are used to assemble oligonucleotides in which there is at least one of the forenoted nucleosides. These sugar modified oligonucleotides have the potential to be used as antisense therapies since they are expected to enhance nuclease resistance and cellular uptake while they maintain sequence-specificity and affinity to nucleic acid targets in vitro or in vivo.

3 Claims, 14 Drawing Sheets

* 5-(R)-Isomers were subjected to the same conversions.

TBDMSM = t-butyldimethylsiloxymethyl

MPM = p-methoxybenzyl

SEQUENCE LISTING (1) GENERAL INFORMATION:

(iii) NUMBER OF SEQUENCES: 2

(2) INFORMATION FOR SEQ ID NO:1:

(i) SEQUENCE CHARACTERISTICS:
       (A) LENGTH: 18 base pairs
       (B) TYPE: nucleic acid
       (C) STRANDEDNESS: unknown
       (D) TOPOLOGY: unknown (ii) MOLECULE TYPE: DNA (other nucleic acid)

(xi) SEQUENCE DESCRIPTION: SEQ ID NO:1:

TTCCTGTCTG ATGGCTTC                                           18

(2) INFORMATION FOR SEQ ID NO:2:

(i) SEQUENCE CHARACTERISTICS:
       (A) LENGTH: 18 base pairs
       (B) TYPE: nucleic acid
       (C) STRANDEDNESS: unknown
       (D) TOPOLOGY: unknown (ii) MOLECULE TYPE: DNA (other nucleic acid)

(xi) SEQUENCE DESCRIPTION: SEQ ID NO:2:

ATCTCTCCGC TTCCTTTC                                           18

SUGAR MODIFIED NUCLEOSIDES

This application is a divisional of application Ser. No. 08/552,363 filed Nov. 2, 1995, now U.S. Pat. No. 5,712,378, which is a continuation in part of Ser. No. 08/333,545 filed Nov. 2, 1994 now U.S. Pat. No. 5,681,940.

FIELD OF THE INVENTION

The invention is in the field of polynucleotide analogs containing modified sugars.

BACKGROUND OF THE INVENTION

The therapeutic use of oligonucleotides is a field of great significance and is described, for example, in, (1) Zamecnik, P. C. and Stephenson, M. L. *Proc. Natl. Acad. Sci. U.S.A.* 1978, 75, 280, 285."; (2) Uhlmann, E. and Peyman, A. *Chemical Reviews*, 1990, 90, 543–584; (3) Goodchild, J. *Bioconjugate chemistry*, 1990, 1, 165–187; and (4) Crooke, S. T. and Lebleu, B. *"Antisense Research and Applications"*, CRC Press (1993)). The specific binding of antisense polynucleotides to the DNA or RNA targets of interest may inactivate the functions associated with the DNA or RNA such as replication, transcription, or translation, thereby providing a mechanism for controlling diseases such as cancer and viral infection. Therefore, the binding of an antisense oligonucleotide to a target can be used to alter gene expression, in a variety of circumstances, e.g., to interfere with viral life cycles, or the growth of cancerous cells (Stein, C. A., Cheng, Y. C. *Science,* 1993, 261, 1004–1012). In addition, some oligonucleotides also bind tightly to protein targets, thereby acting as enzyme inhibitors. Bock et al. describes oligonucleotides that inhibit human thrombin-catalyzed fibrin-clot formation in vitro (Bock, L. C., Griffin, L. C., Latham, J. A., Vermaas, E. H., Toole, J. J. *Nature,* 1992, 355, 564–566). Ecker et al describes several oligonucleotides that inhibit human herpes simplex virus at below 1.0 µmol. Polynucleotides that have enzyme inhibiting properties can readily be found by using combinatorial technology (Ecker, D. J., Vickers, T. A., Hanecak, R., Driver, V., Anderson, K. *Nucleic Acids Res.* 1993, 21, 1853–1856).

An oligonucleotide containing a 5'-C-methyl branched nucleoside has been reported to show enhanced nuclease resistance (Saha, A. K. et al., a poster in 206th ACS Meeting, Chicago, 1993). An oligonucleotide containing 2'-O-methyl nucleosides has also been reported to show improved stability to nucleases and enhanced binding affinity to RNA (a. Inoue, H., Hayase, Y., Imura, A., Iwai, S., Miura, K., Ohtsuka, E., *Nucleic Acids Res.* 1987, 15, 6131; b. Shibahara, S., Mukai, S., Morisawa, H., Nakashima, H., Cobayashi, S., Yamamoto, N. *Nucleic Acids Res.* 1989, 17, 239). An oligonucleotide containing 1'-substituted nucleoside has been reported to show some nuclease resistance (Ono, A., Dan, A., Matsuda, A. Bioconjugate Chemistry, 1993, 4, 499–508).

Besides having a specific binding affinity to a complementary target polynucleotide sequence, antisense oligonucleotides desirably meet the requirements for therapeutic purposes, e.g., potency, bioavailability, low toxicity, and low cost. Since oligonucleotides having the natural phosphodiester backbone are labile to nucleases and do not readily penetrate the cell membrane, researchers have attempted to make polynucleotide backbone modifications that improve nuclease resistance and cellular uptake. A major shortcoming of oligonucleotides analogs used for antisense is that the modified internucleotide linkages eliminate the RNase H activation of antisense oligonucleotides, which degrades the RNA strand to which the oligonucleotide analog binds. Therefore, it is desirable to provide polynucleotide analogs with enhanced nuclease resistance and cellular uptake, while retaining the property of activating RNase H.

SUMMARY OF THE INVENTION

The present invention provides various novel sugar modified nucleosides and corresponding sugar modified oligonucleotides that have properties superior to natural RNA and DNA oligonucleotides when used for antisense, diagnostic, or other purposes.

The compounds of the invention include various nucleosides that have been modified so as to comprise substitutions at positions C1', C3', C4' or C5' of the sugar moiety of the nucleoside.

Another aspect of the invention is to provide oligonucleotides that comprise one or more of the sugar modified nucleosides of the invention.

Another aspect of the invention is to provide conjugates of oligonucleotides that comprise one or more of the sugar modified nucleosides of the invention.

ABBREVIATIONS AND DEFINITIONS

Figure 1:
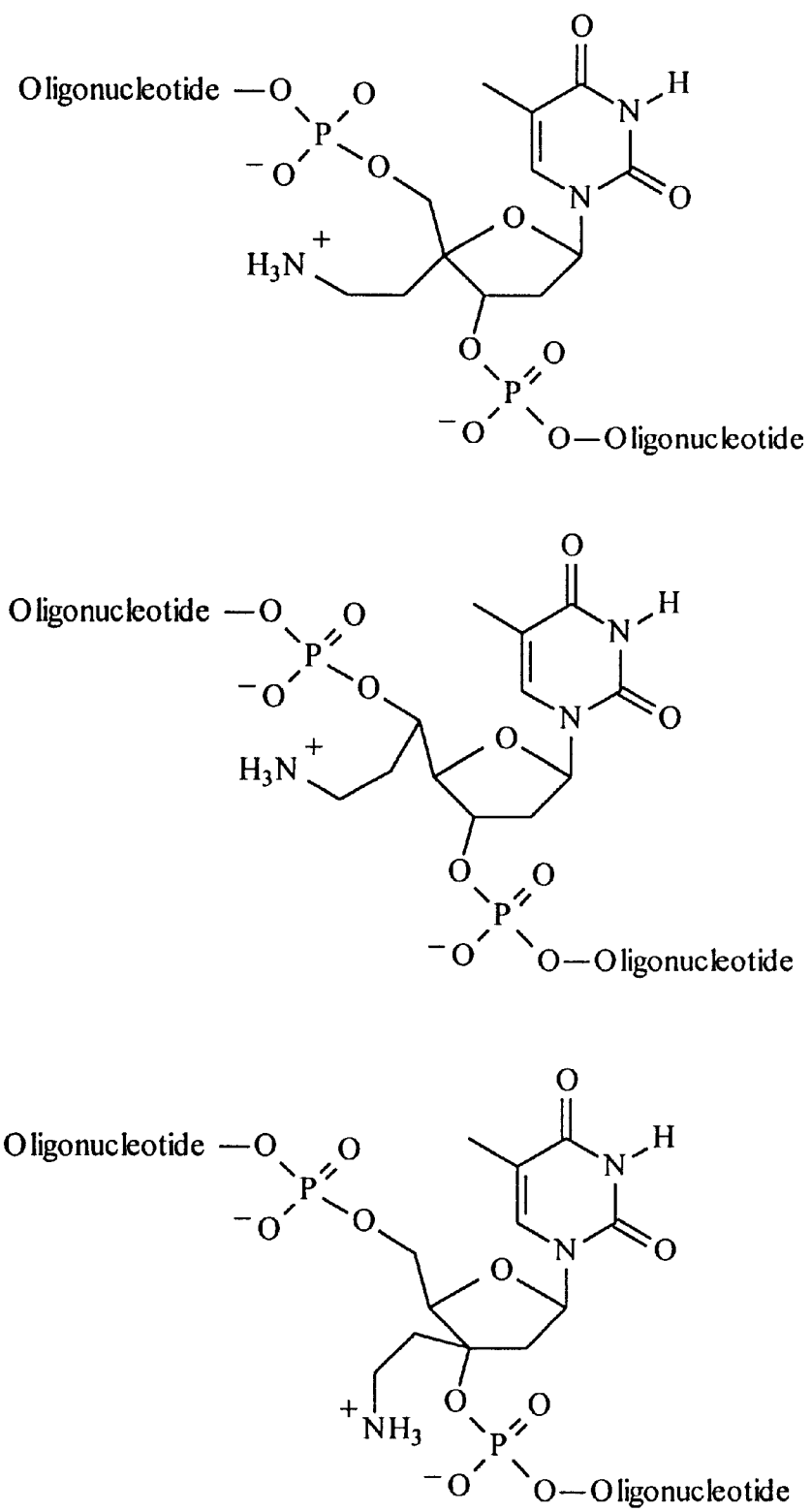
FIG. 1 shows embodiments of the oligonucleotides of the invention in which the nucleoside substituents are substituted with a positively charged moiety.

DMTr=4,4'-dimethoxytrityl
CEPA=2-cyanoethyl-(N,N'-diisopropyl)phosphoramido
TBDMS=t-butyldimethylsilyl
Ac=acetyl
TBDMSM=t-butyldimethylsiloxymethyl
$N_3$=azido
$CF_3CO$=trifluoroacetyl Tf=trifluoromethanesulfonyl
THP=tetrahydropyranyl
OTs=tosyl The term "nucleoside," as used herein, refers to a compound comprising a purine or pyrimidine base (or derivative thereof) covalently joined to a 5 carbon cyclic sugar (furanose), e.g. ribose, 2'-deoxyribose, and 2'3'-dideoxyribose. The term "nucleoside" is used broadly so as to include the sugar modified nucleosides of the invention.

The term "polynucleotide," as used herein, refers to polymers comprising two or more nucleoside moieties, wherein each nucleoside moiety is joined to one (terminal) or two (internal) other nucleoside moieties through internucleoside linkages such as phosphodiester linkages, peptide linkages, phosphonate linkages, phosphorothioate linkages, and the like-RNA and DNA are examples of polynucleotides. The term "polynucleotide", as used herein, unless noted otherwise, is used broadly so as to include the sugar modified polynucleotides of the invention.

The term "oligonucleotide", as used herein, is to refer to relatively small polynucleotides, e.g. polynucleotides of between 2 and about 50 base pairs in length; however oligonucleotide may be significantly longer.

The term "hydroxyl blocking group" as used herein is readily understood by the person of ordinary skill in the art of organic chemistry. Examples of hydroxyl blocking groups, and other blocking groups, can be found (among other places) in Greene and Wuts, "Protective Groups in Organic Synthesis" John Wiley & Sons, NY, N.Y. (1991).

The terms "base" and nucleoside base" as used herein refer to heterocyclic nucleotide bases found in naturally occurring nucleic acid such as adenine, cytosine, hypoxanthine, uracil, thymine, guanine and analogs thereof, including non-naturally occurring bases that are capable of forming base-pairing relationships with naturally occurring nucleotide bases. Such non-naturally occurring heterocyclic bases include, but are not limited to, aza and deaza pyrimidine analogs, aza and deaza purine analogs as well as other heterocyclic base analogs, wherein one or more of the carbon and nitrogen atoms of the purine and pyrimidine rings have been substituted by heteroatoms, e.g. oxygen, sulfur, selenium, phosphorus, and the like.

DESCRIPTION OF THE SPECIFIC EMBODIMENTS

The subject invention provides novel nucleosides and oligonucleotide having desirable properties for use in antisense, diagnostic, and other methods employing oligonucleotides. The compounds of the invention include various nucleosides that have been modified so as to comprise substitutions at position C1', C3', C4' or C5' of the sugar moiety of the nucleoside. The nucleosides of the invention may comprise one or more substitutions so as to adapt the nucleoside for solid phase synthesis or related synthetic techniques, e.g., the subject nucleosides may be in a phosphoramidite derivative with 5'-dimethoxytrityl or other protecting groups. The subject invention also provides oligonucleotides comprising one or more of the sugar modified nucleosides of the invention in a nucleic acid chain.

Adding a suitable substituent at positions C3' or C5' of a nucleoside changes the environment around the phosphodiester backbone of oligonucleotides containing these sugar modified nucleosides. Preferably, a bulky substituent at C3' or C5' is used to inhibit unwanted interactions with enzymes or their active sites. These C3' or C5' substituents are predicted to make the phosphodiester backbone of oligonucleotides inaccessible to many enzymes. As result of the presence of the substituents, oligonucleotides containing these C3' or C5' branched nucleosides may be more nuclease resistant, as compared with DNA or RNA. Substituents at the C1' and C4' positions of nucleosides may exert the same desirable effects as those at C3' and C5' position of nucleosides. In those embodiments of the invention where the subject oligonucleotides comprise positively charged aminoalkyl modified sugars, the net negative charges on the subject oligonucleotides at the physiological conditions are reduced so that the double helix formed by at least one strand of these oligonucloetides can be more stable than a corresponding unmodified oligonucleotide (see FIG. 1). Thus, in those embodiments of the invention comprising aminoalkyl modified sugars, or similar positively charged substituents, the binding affinity between the subject oligonucleotides and a polynucleotide hybridization target may be improved by the positive charge. It will be appreciated by a person of ordinary skill in the art that the above stated theories, while providing guidance in the use and design of additional embodiments of the invention, need not be correct in order to make or use the invention provided herein.

One embodiment of the invention is sugar modified nucleosides having the formula:

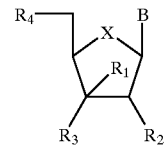

(45)

Where $R_1$ may be alkyl, aralkyl, aryl, substituted alkyl, substituted aralkyl, substituted alkyl, substituted aryl, where the substituents may be $NO_2$, CN, $N_3$, COOEt, OH, SR, $CONH_2$, CONHR, $CONR_2$, COOH, OAC, $NH_2$, NHAc, $NMe_2$, $CF_3CONH$, OR, SR, $SO_2CH_3$, $CF_3$, F, Cl, Br, I, OTs, $^+NMe_3$, CH=CHR, C=CR, where R is alkyl; $R_2$ may be H, OH, alkoxy, aryloxy; $R_3$ may be OH, O-CEPA; $R_4$ may be OH or a hydroxyl blocking group; B is a heterocyclic nucleoside base; X may be O, or $CH_2$.

The heterocyclic nucleoside base, B, of the sugar modified nucleosides of the invention, as represented in formulae 45, 46, 47, 48, 49, and 50, may be any heterocyclic nucleoside base, either naturally occurring or non-naturally occurring. Thus, heterocyclic nucleoside bases that may be base moieties in the sugar modified nucleosides of the invention may be purines (e.g., adenine, guanine, or xanthine), pyrimidines (e.g., thymine, uracil, cytosine), and heterocyclic analogs and tautomers thereof. Suitable heterocyclic bases that may serve as the base moiety of the nucleoside compounds of the invention are those bases that may be incorporated into one strand of a double-stranded polynucleotide so as to maintain a base pairing structural relationship with a naturally occurring base on the complementary strand of the polynucleotide. Additionally, the base moiety of the nucleoside compounds of the invention are joined to the sugar moiety at a site on the base that permits the base to enter into base pairing relationships, as previously discussed.

Another embodiment of the invention is to provide nucleotides having the formula:

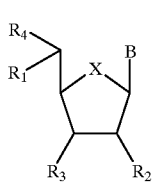

(46)

Where R₁ may be alkyl, aralkyl, aryl, substituted alkyl, substituted aralkyl, substituted alkyl, substituted aryl, where the substituents may be $NO_2$, CN, $N_3$, COOEt, OH, SH, $CONH_{21}$ CONHR, $CONR_2$, COOH, OAC, $NH_2$, NHAc, $NMe_2$, $CF_3CONH$, OR, SR, $SO_2Me$, $CF_3$, F, Cl, Br, I, OTs, $^+NMe_3$, CH=CHR, C≡CR, where R is alkyl; $R_2$ may be H, OH, alkoxy, aryloxy; $R_3$ may be OH, O-TBDMS, O-CEPA; $R_4$ may be OH, CHO, or a hydroxyl blocking group; B is a heterocyclic nucleoside base; X may be O or $CH_2$; wherein the carbon attached to both $R_1$ and $R_4$ is either R or S configuration.

Another embodiment of the invention is nucleosides having the formula:

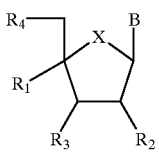

(47)

where $R_1$ may be alkyl, aralkyl, aryl, substituted alkyl, substituted aralkyl, substituted alkyl, substituted aryl, where the substituents may be $NO_2$, CN, $N_3$, COOEt, OH, SH, $CONH_2$, CONHR, $CONR_2$, COOH, OAC, $NH_2$, NHAc, $NMe_2$, $CF_3CONH$, OR, SR, $SO_2Me$, $CF_3$, F, Cl, Br, I, OTs, $^+NMe_3$, CH=CHR, C≡CR, where R is alkyl; $R_2$ may be H, OH, alkoxy, aryloxy; $R_3$ may be OH, OTBDMS, O-CEPA; $R_4$ may be OH or a hydroxyl blocking group; B is a heterocyclic nucleoside base; X may be O or $CH_2$.

Another aspect of the invention is to provide nucleotides having the formula:

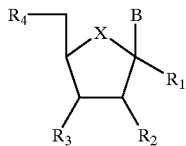

(48)

where $R_1$ may be alkyl, aralkyl, aryl, substituted alkyl, substituted aralkyl, substituted alkyl, substituted aryl, where the substituents may be $NO_2$, CN, $N_3$, COOEt, OH, SH, $CONH_2$, CONHR, $CONR_2$, COOH, OAC, $NH_2$, NHAc, $NMe_2$, $CF_3CONH$, OR, SR, $SO_2Me$, $CF_3$, F, Cl, Br, I, OTs, $^+NMe_3$, CH=CHR, C≡CR, where R is alkyl; $R_2$ may be H, OH, alkoxy, aryloxy; $R_3$ may be OH, O-MBn, O-CEPA; $R_4$ may be OH, or a hydroxyl blocking group; B is a heterocyclic nucleoside base; X may be O or $CH_2$.

Another aspect of the invention is to provide various epoxide derivatives of the sugar modified nucleosides of the invention having the formulae:

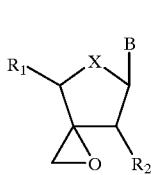

(49)

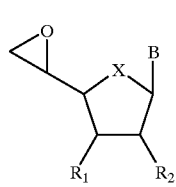

(50)

where R is selected from the group consisting of $CH_2OH$, $CH_2ODMTr$, CHO, COOH, and CoOEt; and X is selected from the group consisting of O and $CH_2$. The epoxides may be in either of the two possible stereochemical orientations.

The sugar modified nucleoside of the invention may be synthesized by reference to the examples provided in the examples section of this application. A person of ordinary skill in the art of organic chemistry may, given the example provided herein, synthesize numerous compounds of the invention for which explicit syntheses are not given.

Oligonucleotides containing Sugar Modified Nucleosides

The polynucleotides of the invention comprise one or more of the sugar modified nucleosides of the invention, wherein a sugar modified nucleoside of the invention is joined to either a second sugar modified nucleoside or an unmodified nucleoside, wherein the nucleosides are joined through an internucleoside linkage. The sugar modified nucleosides for incorporation into the oligonucleotides of the invention include the compounds of formulae 45, 46, 47, and 48. The polynucleotide analogs of the invention are not limited with respect to the number of possible nucleoside subunits in an individual polynucleotide analog; however, it is generally more convenient to synthesize short polynucleotide analogs, e.g., polynucleotides analogs comprising less than 50 bases.

The individual nucleosides of the invention may be joined to one another through internucleoside linkages so as to produce novel oligonucleotides having desired nucleoside base sequences. The internucleoside linkages may be C3' to C5' linkage or a C2' to C5' linkage. The term "internucleoside linkage" as used herein refers not only to the phosphodiester backbone of the type that forms internucleoside linkages in DNA (dideoxyribonucleic acid) and RNA (ribonucleic acid), but also to a variety of other moieties that serve the same structural function as phosphodiester linkages in DNA and RNA. Examples of other internucleoside linkages suitable for the oligonucleotides of the invention include phosphorothioates, methylphosphonates, phosphorodithioates, boron phosphonates, selenophosphonates, phosphoramidates, acetamidates, and the like. Descriptions of the synthesis and use of various internucleoside linkages can be found, among other places in U.S. Pat. No. 5,256,775, PCT Publication WO93/24507, PCT Publication WO92/05186, U.S. Pat. No. 5,264,562, PCT Publication WO92/02534, PCT Publication W094/06811, PCT Publication WO93/17717, U.S. Pat. No. 5,212, 295, U.S. Pat. No. 5,292,875, U.S. Pat. No. 5,218,103, U.S. Pat. No. 5,166,387, U.S. Pat. No. 5,151,516, U.S. Pat. No.

4,814,448, U.S. Pat. No. 4,814,451, U.S. Pat. No. 4,096,210, U.S. Pat. No. 4,094,873, U.S. Pat. No. 4,092,312, U.S. Pat. No. 4,016,225, U.S. Pat. No. 4,007,197, and the like.

Polynucleotides of the invention having a desired base sequence may readily be produced using nucleic acid polymer synthesis techniques that are well known to the person of ordinary skill in the art of organic chemistry. The polynucleotides of the invention are preferably synthesized using phosphoramidite chemistry to incorporate one or more of the novel nucleoside of the invention into a polynucleotide analog. Branched substituents at C3' or C5' of the nucleosides of the invention may reduce the coupling rate, depending on the size of the substituents. Therefore, for some bulky substituent branched nucleosides, coupling time may need to be extended to up to 10 times or more. The repeated couplings with fresh reagents and use of more concentrated coupling reagents may also be used to increase the rate of the coupling reaction, when necessary. After synthesis oligonucleotides may be worked up in the same way as standard unmodified oligonucleotide, that is, cleaving from solid supports by using 30% ammonia, deprotection under 55° C. for 8 h, and purified by reverse phase HPLC.

In order to verify both the purity of oligonucleotides and incorporation of desired sugar modified nucleosides, the purified oligonucleotides may be characterized by analysis of enzyme digestion products using enzymes such as snake venom phosphodiesterase and bacterial alkaline phosphatase to degrade the oligonucleotides. The degraded products may then be subjected to HPLC analysis (or other separation techniques) and comparison with the authentic nucleoside samples. The structure of purified oligonucleotides can also be verified by mass spectroscopy such as electrospray technique.

Another aspect of the invention is conjugates of the sugar modified oligonucleotides of the invention. Amino-, hydroxy, thio-, or carboxylalkyl linkers may be attached to the C1', C3', C4', and C5' position of the subject nucleosides so as to provide a site for conjugating a moiety of interest to the oligonucleotide. Linkers attached to positions C1' and C3' may be used to direct the conjugating moiety to the minor grooves of a double stranded nucleic acid, while linkers attached to position C4' may be used to direct the conjugating moiety to the major grooves. Linkers attached to position C5' may be used to direct a conjugate moiety to either the major or minor grooves of a double stranded nucleic acid, depending on the stereochemistry of the linker at C5'. Through linkers, a wide variety of functional moieties such as artificial nuclease, crosslinking reagents, intercalators, and reporter molecules can be linked to and located in the desired position.

Utility and Administration

As the oligonucleotides of the invention are capable of significant single-stranded or double-stranded target nucleic acid binding activity to form duplexes, triplexes or other forms of stable association, with naturally occurring polynucleotides and structural analogs thereof, the oligonucleotides of the invention may be used in most procedures that employ conventional oligonucleotides. Thus, the oligonucleotides of the invention may be used as, for example, polynucleotide hybridization probes, primers for the polymerase chain reaction (and similar cyclic amplification reactions), sequencing primers, and the like. The oligonucleotides of the invention may also be used in the diagnosis and therapy of diseases. Therapeutic applications of the oligonucleotides of the invention include the specific inhibition of the expression of genes (or the inhibition of translation of RNA sequences encoded by those genes) that are associated with either the establishment or the maintenance of a pathological condition through the use of antisense oligonucleotides. The oligonucleotides of the invention may be used to mediate antisense inhibition of numerous genetic targets. Exemplary genes or RNAs encoded by those genes that may be targeted through antisense oligonucleotides of the invention include oligonucleotides that encode enzymes, hormones, serum proteins, transmembrane proteins, adhesion molecules (LFA-1, $GPII_b/III_a$, ELAM-1, VACM-1, ICAM-1, E-selection, and the like), receptor molecules including cytokine receptors, cytokines (IL-1, IL-2, IL-3, IL-4, IL-6 and the like), oncogenes, growth factors, and interleukins. Target genes or RNAs may be associated with any pathological condition such as those associated with inflammatory conditions, cardiovascular disorders, immune reactions, cancer, viral infections, bacterial infections, yeast infections, parasite infections and the like.

Oligonucleotides of the present invention are suitable for use in both in vivo and ex vivo therapeutic applications. Indications for ex vivo uses include treatment of cells such as bone marrow or peripheral blood in conditions such as leukemia (chronic myelogenous leukemia, acute lymphocytic leukemia) or viral infection. Target genes or RNAs encoded by those genes that may serve as targets for cancer treatments include oncogenes, such as ras, k-ras, bcl-2, c-myb, bcr, c-myc, c-abl or overexpressed sequences such as mdm2, oncostatin M, IL-6 (Kaposi's sarcoma), HER-2 and translocations such as bcr-abl. Viral gene sequences or RNAs encoded by those genes such as polymerase or reverse transcriptase genes of herpesviruses such as CMV, HSV-1, HSV-2, retroviruses such as HTLV-1, HIV-1, HIV-2, or other DNA or RNA viruses such as HBV, HPV, VZV, influenza virus, adenoviruses, flaviviruses, rhinovirus and the like are also suitable targets. Application of specifically binding oligonucleotides may be used in conjunction with other therapeutic treatments. Other therapeutic uses for oligonucleotides of the invention include (1) modulation of inflammatory responses by modulating expression of genes such as IL-1 receptor, IL-1, ICAM-1 or E-Selection that play a role in mediating inflammation and (2) modulation of cellular proliferation in conditions such as arterial occlusion (restenosis) after angioplasty by modulating the expression of (a) growth or mitogenic factors such as non-muscle myosin, myc, fox, PCNA, PDGF or FGF or their receptors, or (b) cell proliferation factors such as c-myb. Other suitable proliferation factors or signal transduction factors such as TGFa, IL-6, gINF, protein kinase C, tyrosine kinases (such as p210, p190), may be targeted for treatment of psoriasis or other conditions. In addition, EGF receptor, TGFa or MHC alleles may be targeted in autoimmune diseases.

The oligonucleotides of the invention may also be advantageously substituted for conventional oligonucleotides in many non-therapeutic techniques such as hybridization to detect nucleic acid sequences, the polymerase chain reaction, and the like. These non-therapeutic techniques are well known to the person of ordinary skill in the art of molecular biology and can be found, for example, in Sambrook et al. *Molecular Cloning Techniques* 2nd Edition Clod Spring Harbor (1989).

Delivery of oligonucleotides of the invention into cells may be enhanced by any suitable method including calcium phosphate, DMSO, glycerol or dextran transfection, electroporation or by the use of cationic anionic and/or neutral lipid compositions or liposomes by methods described (International Publications Nos. WO 90/14074, WO 91/16024, WO 91/17424, U.S. Pat. No. 4,897,355). The oligonucleotides may be introduced into cells by complexion with cationic lipids such as DOTMA (which may or may not form liposomes) which complex is then contacted with the cells. Suitable cationic lipids include but are not limited to N-(2,3-di(9-(Z)-octadecenyloxyl))-prop-1-yl-N,N,N-trimethylammonium (DOTMA) and its salts, 1-O-oleyl-2-O-oleyl-3-dimethylaminopropyl-β-hydroxyethylammonium and its salts and 2,2-bis (oleyloxy)-3-(trimethylammonio) propane and its salts.

Enhanced delivery of the invention oligonucleotides may also be mediated by the use of (i) viruses such as Sendai virus (Bartzatt, R., *Biotechnol Appl Biochem.*, 1989, 11,133–135) or adenovirus (Wagner, E. et al, *Proc Natl Acad Sci. USA*, 1992, 89, 6099–6013); (ii) polyamine or polycation conjugates using compounds such as polylysine, protamine or Na, $N_{12}$-bis (ethyl)spermine (Wagner, E. et al, *Proc Natl Acad Sci. USA*, 1991, 88, 4255–4259; Zenke, M. et al, *Proc. Natl. Acad. Sci. USA*, 1990, 87, 3655–3659; Chank, B. K. et al, *Biochem Biophys Res Commun.*, 1988, 157, 264–270; U.S. Pat. No. 5,138,045); (iii) lipopolyamine complexes using compounds such as lipospermine (Behr, J. -P. et al, *Proc Natl Acad Sci. USA*, 1989, 86, 6982–6986; Loeffler, J. P. et al, *J. Neurochem.*, 1990, 54, 1812–1815); (iv) anionic, neutral or pH sensitive lipids using compounds including anionic phospholipids such as phosphatidyl glycerol, cardiolipin, phosphatidic acid or phosphatidyl-ethanolamine (Lee, K. -D. et al, *Biochem Biophys ACTA*, 1992, 1103, 185–197; Cheddar, G. et al, *Arch Biochem Biophys*, 1992, 294, 188–192; Yoshimura, T., et al, *Biochem Int.*, 1990, 20, 697–706); (v) conjugates with compounds such as transferrin or biotin or (vi) conjugates with proteins (including albumin or antibodies), glycoproteins or polymers (including polyethylene glycol) that enhance pharmacokinetic properties of oligonucleotides in a subject. As used herein, transfection refers to any method that is suitable for delivery of oligonucleotides into cells. Any reagent such as a lipid or any agent such as a virus that may be used in transfection protocols is collectively referred to herein as a "permeation enhancing agent". Delivery of the oligonucleotides into cells may be via cotransfection with other nucleic acids such as (i) expressable DNA fragments encoding a protein(s) or a protein fragment or (ii) translatable RNAs that encode a protein(s) or a protein fragment.

The oligonucleotides of the invention may thus be incorporated into any suitable formulation that enhances delivery of the oligonucleotides into cells. Suitable pharmaceutical formulations also include those commonly used in applications where compounds are delivered into cells or tissues by topical administration. Compounds such as polyethylene glycol, propylene glycol, azone, nonoxonyl-9, oleic acid, DMSO, polyamines or lipopolyamines may be used in topical preparations that contain the oligonucleotides.

Synthesis of 3'-C-branched Nucleosides

Figure 2:
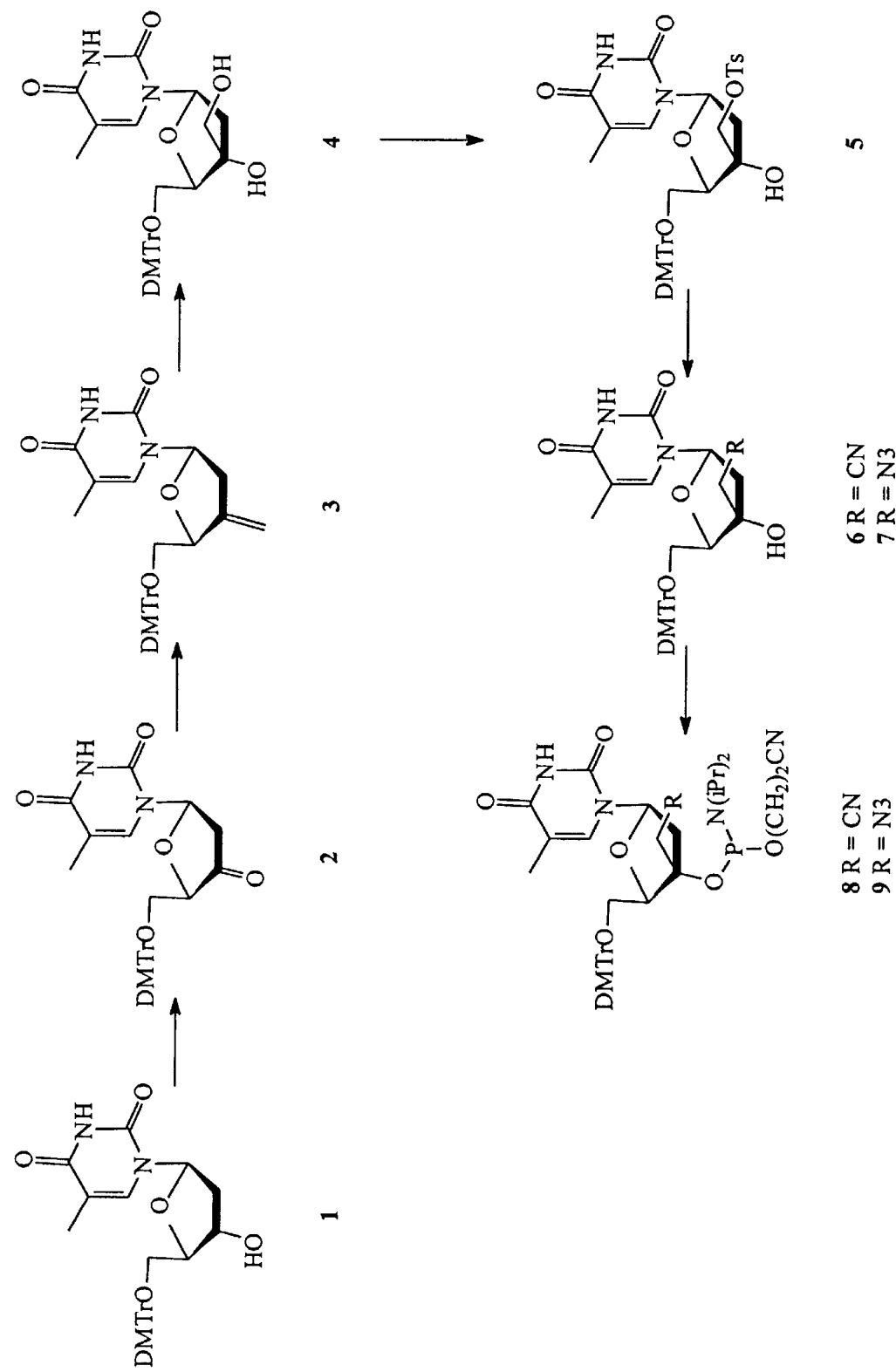
FIG. 2 shows reaction scheme 1, for the synthesis of 3'-C-branched thymidine.
Figure 3:
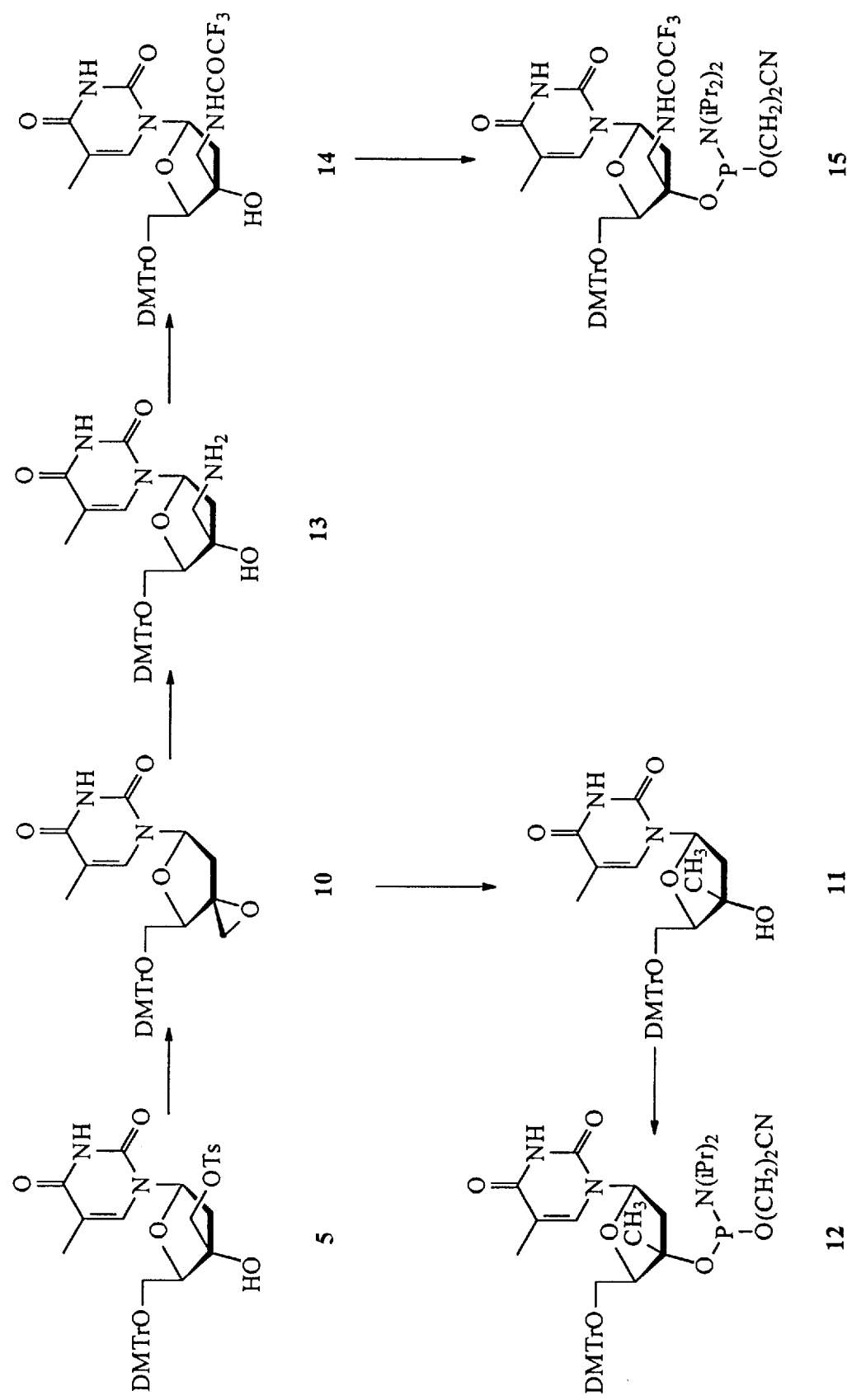
FIG. 3 shows reaction scheme 2, for the synthesis of 3'-C-branched thymidine.
Figure 4:
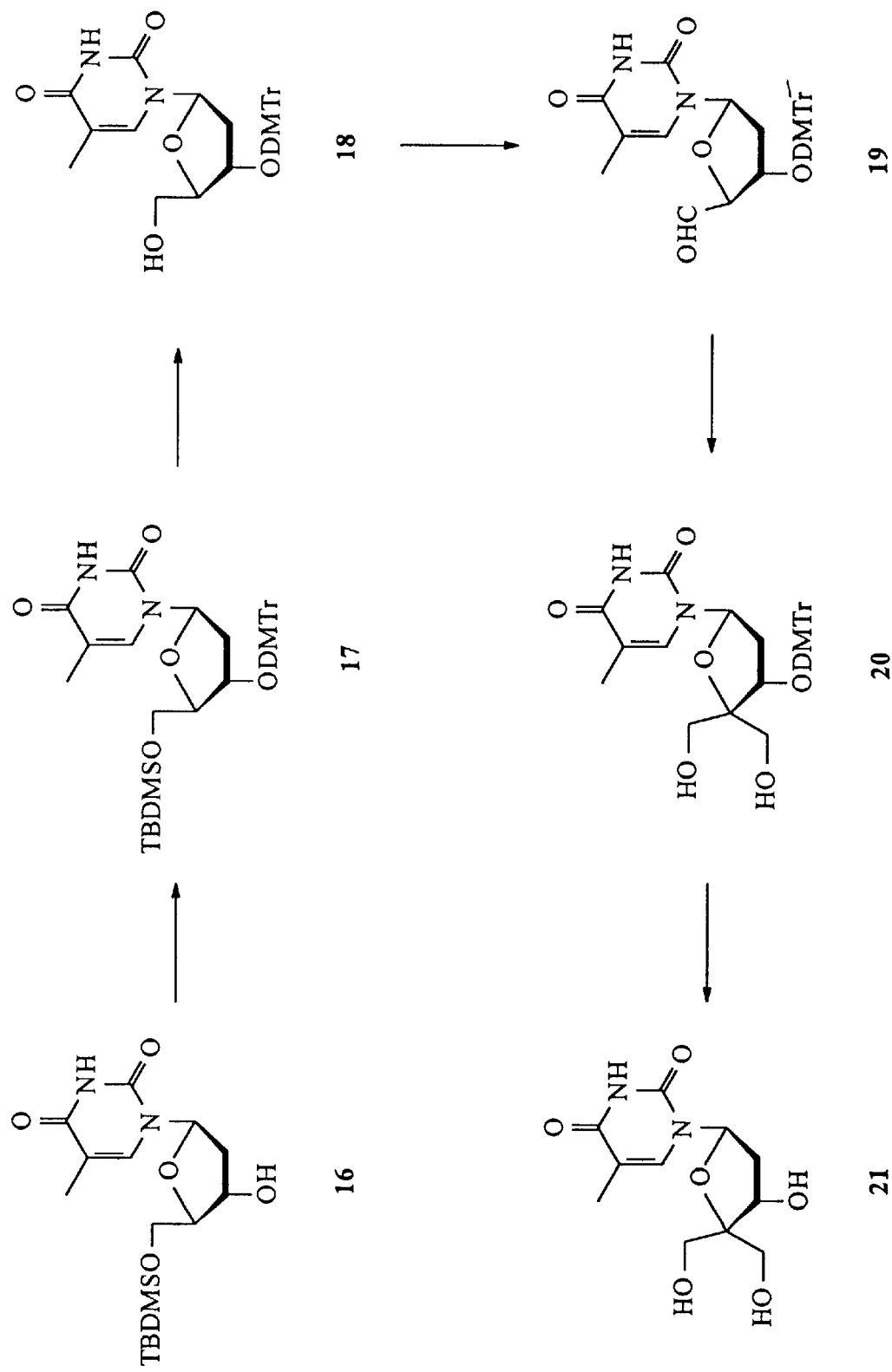
FIG. 4 shows reaction scheme 3, for the synthesis of 4'-C-branched thymidine.
Figure 5:
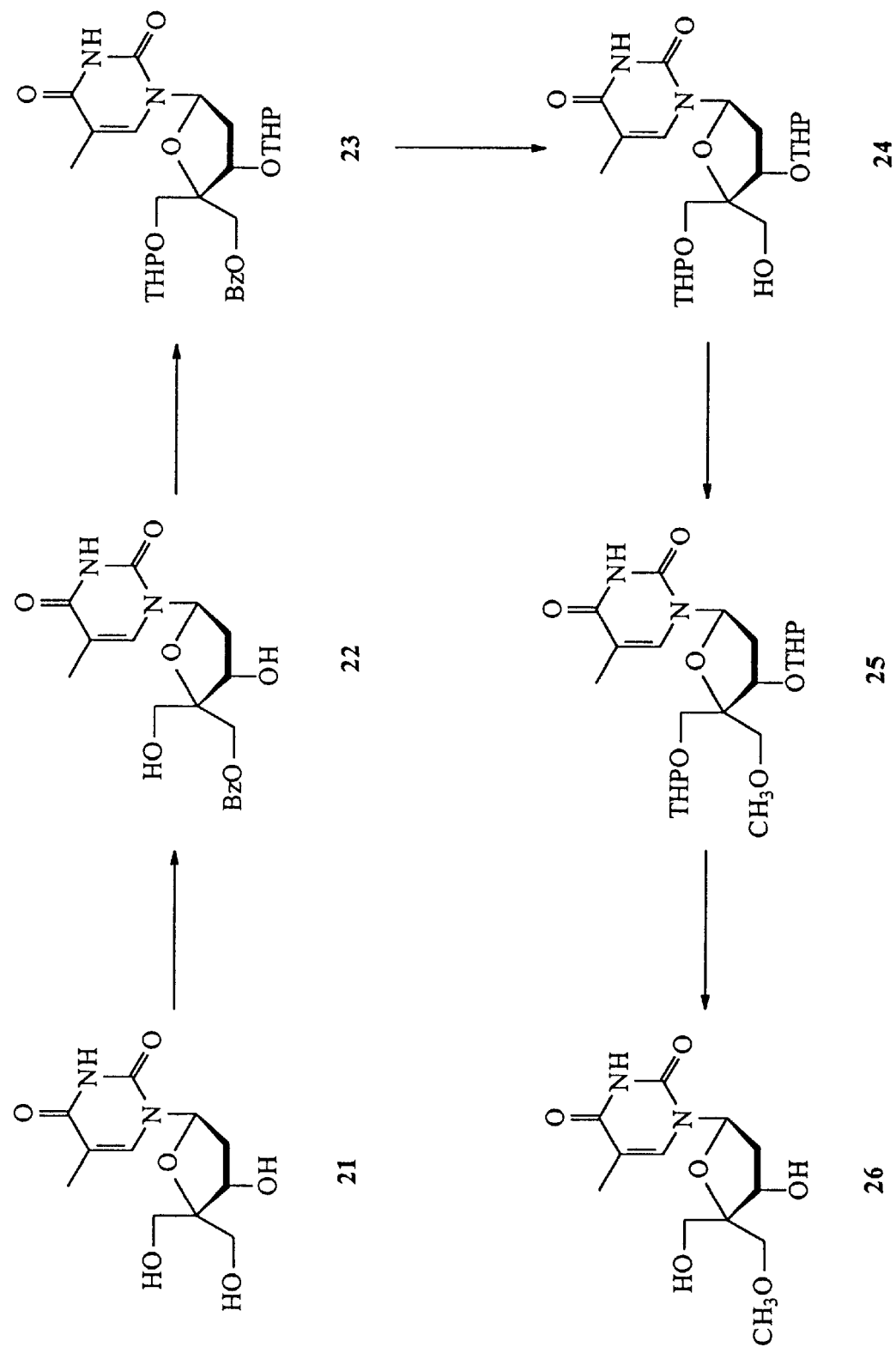
FIG. 5 shows additional aspects of reaction scheme 3, for the synthesis of 4'-C-branched thymidine.
Figure 6:
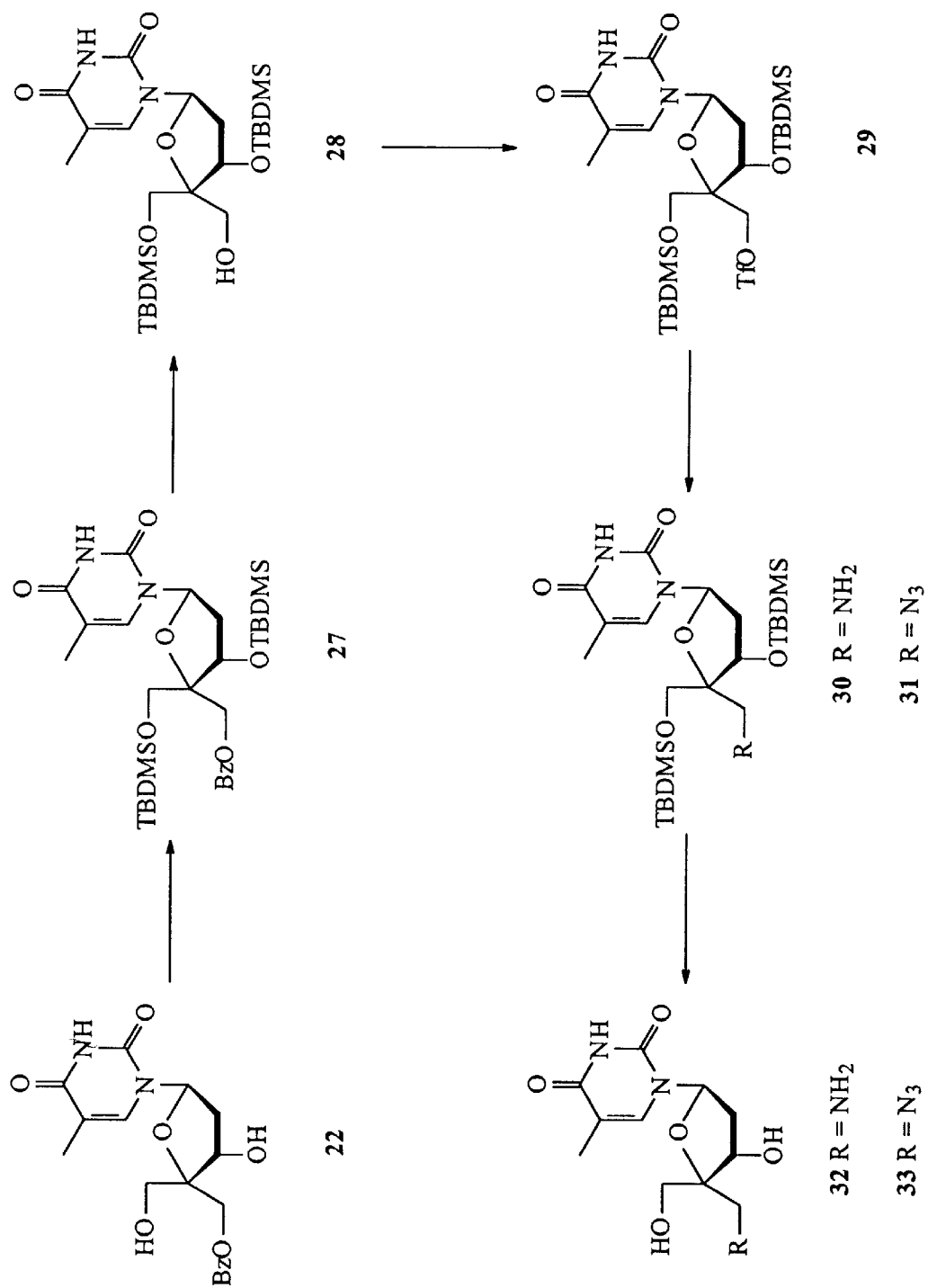
FIG. 6 shows reaction scheme 4, for the synthesis of 4'-C-branched thymidine.
Figure 7:
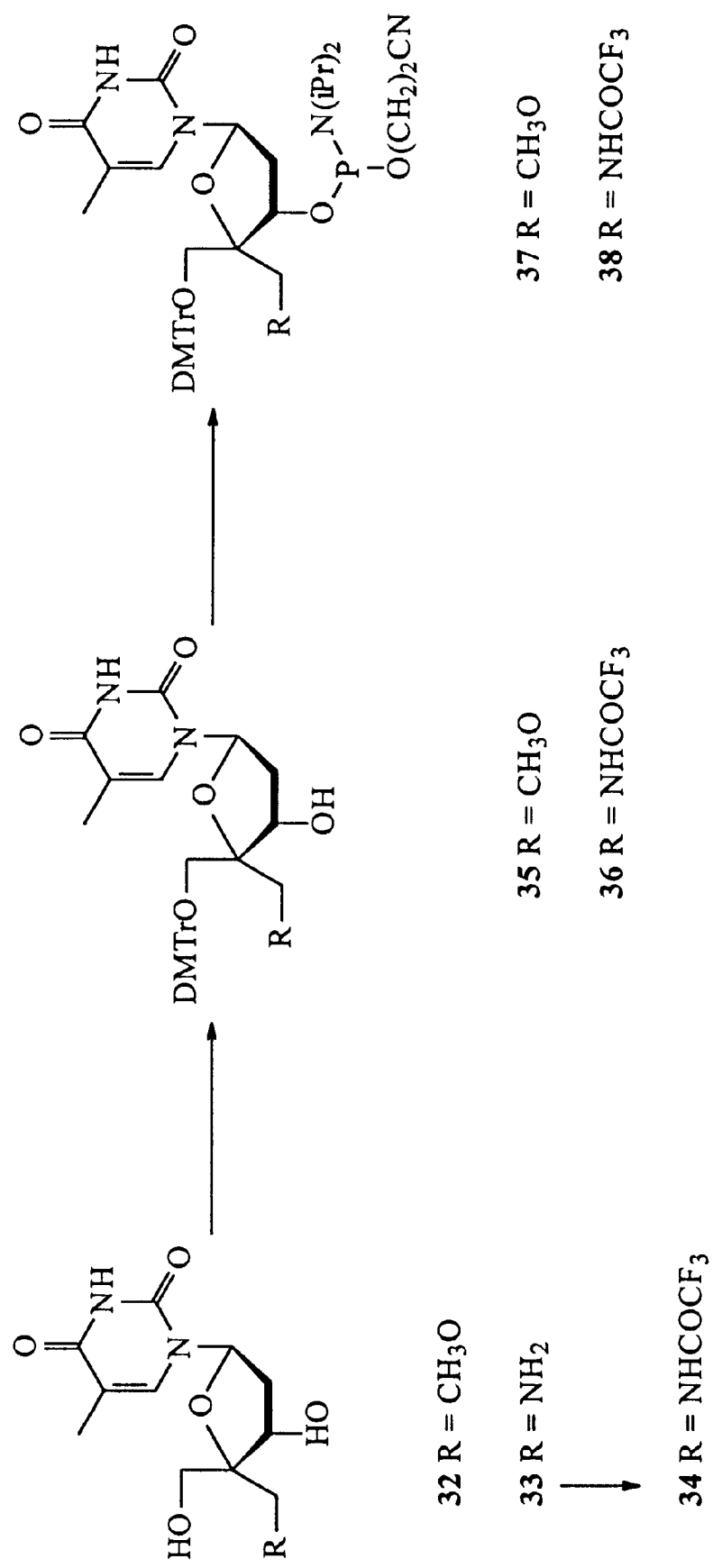
FIG. 7 shows reaction scheme 5, for the synthesis of 5'-C-branched thymidine.

Hydroxyl group substitution at C3' of nucleosides by other functional groups with preservation of hydrogen at C3' position has been described in, among other places, De Clercq, E., *Antiviral Res.* 1989, 12, 1–20. Hydrogen substitution at C3' of nucleosides by other functional groups has been reported in Fedorov, I. I., Kazmina, E. M., Novicov, N. A., Gurskaya, G. V., Bochkarev, A. V., Jasko, M. V., Victorova, L. S., Kuhkanova, M. K-, Balzarini, J., De Clercq, E. *J. Med. Chem.* 1992, 35, 4567–4575. This invention provides procedures for the preparation of a large number of different 3'-C-branched nucleosides. Examples of the methods for preparing 3'-C-branched thymidines are shown in Reaction schemes 1 and 2 (FIGS. 2 and 3, respectively). These procedures may be readily adapted for the synthesis of other nucleosides of the invention, including embodiments of the invention in which the nucleosides comprise a base other than thymine. Compound 4 was prepared in three steps from thymidine as described (Jorgensen, P. N., Thrane, H., Wengel, J. *J. Am. Chem. Soc.* 1994, 116, 2231). Treatment of Compound 4 with tosyl chloride in pyridine-afforded a tosylate, Compound 5. Reaction of Compound 5 with potassium cyanide in DMF afforded a 3'-C-cyanomethylthymidine derivative, Compound 6. Reaction of Compound 5 with sodium azide in DMF afforded 3'-C-azidomethyl-thymidine derivative, Compound 7. Similarly, reactions of Compound 5 with a variety of nucleophilic reagents can afford a wide variety of 3'-C-branched thymidine derivatives, in which 3'-C-hydroxyl group remains in the same orientation as in thymidine. Treatment of Compound 6 with 2-cyanoethyl-N, N-diisopropylchlorophosphoramidite and diisopropylethylamine in dichloromethane afforded a phosphoramidite, Compound 8, a building block for oligonucleotide synthesis. Compound 7 was subjected to the same treatment to give Compound 9. Similarly, the other 3'-C-branched thymidine derivatives can be converted to the corresponding phosphoramidites by a standard procedure (F. Eckstein, "*Oligonucleotide Synthesis*", Oxford University Press (1991)). Treatment of Compound 5 with sodium hydride in THF afforded an epoxide derivative, Compound 10. Reaction of Compound 10 with lithium aluminum hydride in THF afforded 3'-C-methylthymidine derivative, Compound 11, which was converted to the phosphoramidite, Compound 12. Reaction of Compound 10 with ammonia in methanol afforded 3'-C-aminomethylthymidine derivative, Compound 13, which was treated with ethyl thiotrifluoroacetate in THF to give a protected amino derivative, Compound 14. Compound 14 was converted to the phosphoramidite, Compound 15. Similarly, Reaction of Compound 10 with a variety of nucleophilic reagents can afford a wide variety of 3'-C-branched thymidine derivatives in which 3'-C-hydroxyl group remains in the same orientation as in thymidine since the nucleophiles attack the less hindered carbon of the epoxide ring. Thus, reaction of Compound 10 with alcohols in the presence of base give alkoxymethylthymidines. Substituted alcohols can also be used to prepare 3'-C-substituted alkoxymethylthymidines. The substituents may include, but not limited to, $NO_2$, CN, COOEt, and protected amino groups. Reaction of Compound 10 with diols affords 3'-C-hydoxyalkoxymethylthymidines, which can be readily converted to 3'-C-haloalkoxymethylthymidines. Reaction of Compound 10 with nitromethane gives 3'-C-nitroethyl thymidine. Reduction of 3'-C-nitroalkylthymidines affords 3'-C-aminoalkylthymidines- Reaction of Compound 10 with cyano-substituted organocadmium reagents gives 3'-C-cyanoalkylthymidines. Reaction of Compound 10 with ethoxycarbonylalkylzinc reagents affords 3'-C-ethoxycarbonyl-alkylthymidines, which are readily hydrolyzed to 3'-C-carboxy-alkylthymidines at basic condition.

For some reactions involving lithium organocuprate reagents, the amide group of thymine may need protection. t-Butyldimethylsiloxymethyl (TBDMSM) is preferred for use as the protecting group since it can be readily removed by tetrabutylammonium fluoride (TBAF) after the subsequent transformations. N-TBDMSM group can be introduced by reaction of 3,5-biacylated thymidne with t-butyldimethylsiloxymethyl chloride in pyridine. N-TBDMSM thymidine is subjected to the similar treatment as described above for thymidine to give a tosylate, a derivative of Compound 5, and an epoxide, a derivative of Compound 10, respectively, both of which can be used to prepare 3'-C-alkylthymidines and 3'-C-alkenyl-thymidines by reaction with lithium reagents. Hydroboration or oxidative cleavage of the resulting 3'-C-(ω-alkenyl) thymidines yields hydroxyalkylthymidines, hydroxyl of which can be converted to a variety of functionalities such as $NH_2$, OR, SR, SH, and X, where R is H, or alkyl, and X is F, Cl, Br, I, OTs.

Synthesis of 4'-C-branched Nucleosides

A number of 4'-C-branched nucleosides have been reported in O-Yang C., Wu, H. Y., Fraser-Smith, E. B., Walker, K. A. M. *Tetrahedron Lett.s,* 1992, 33, 37–40. This invention provides procedures for preparation of many new 4'-C-branched nucleosides. Preparation of 4'-C-branched thymidines is shown in Reaction schemes 3, 4, and 5 (FIGS. 4, 5, 6, and 7, respectively). These procedures may be readily adapted for the synthesis of other nucleosides of the invention, including embodiments of the invention in which the nucleosides comprise a base other than thymine. Compound 16, prepared from thymidine, was treated with dimethoxytrityl chloride to give Compound 17. t-Butyldimethylsilyl (TBDMS) group of Compound 17 was removed by treatment with TBAF to give Compound 18, which was oxidized to an aldehyde, Compound 19 by treatment with dimethyl sulfoxide, DCC, trifluoroacetic acid, and pyridine. Compound 19 was converted to Compound 20, a 4'-C-hydroxy-methylthymidine derivative, by a procedure similar to those as described (a. O-Yang C., Wu, H. Y., Fraser-Smith, E. B., Walker, K. A. M. *Tetrahedron Letts,*1992,33, 37–40; b. Jones, G. H., Taniguchi, M., Tegg, D., Moffatt, J. G. *J. Org. Chem.* 1979, 44, 1309–17). Dimethoxytrityl group of Compound 20 was removed with 80% acetic acid to give Compound 21, 4'-C-hydroxymethyl-thymidine. Selective benzoylation of Compound 21 with benzoyl anhydride affords Compound 22, 3'- and 5'-hydroxyl groups of which were protected with tetrahydropyranyl (THP) by reaction of Compound 22 with dihydropyran in the presence of toluenesulfonic acid in dichloromethane. The resulting Compound 23 was treated with aqueous sodium hydroxide to give Compound 24, which was reacted with methyl iodide in the presence of sodium hydroxide at 0° C. to give a 4'-C-methoxy-methylthymidine derivative, Compound 25. Removal of THP protecting groups of Compound 25 afforded Compound 26, 4'-C-methoxymethylthymidine. For some reactions TBDMS protecting group is preferred to THP because of formation of diastereomers caused by THP. Thus, treatment of Compound 22 with t-butyldimethylchlorosilane afford 3', 5'-O-(bis-TBDMS) thymidine derivative, Compound 27. Removal of benzoyl group with ethylenediamine at 50° C. afforded Compound 28, which reacted with trifluoromethanesulfonic anhydride and pyridine in dichloromethane to give a triflate, Compound 29. Reaction of Compound 29 with ammmonia in dioxane afforded a 4'-C-amino-methylthymidine derivative, Compound 30. Reaction of Compound 29 with sodium azide in DMF afforded a 4'-C-azidomethyl-thymidine derivative, Compound 31. Removal of TBDMS protecting groups of Compound 30 and 31 afforded Compound 32 and 33, 4'-C-aminomethylthymidine and 4'-C-azidomethylthymidine, respectively. Amino group of Compound 33 was protected with trifluoroacetyl group to give Compound 34. Reaction of Compound 32 and 34 with dimethoxytrityl chloride in pyridine afforded Compound 35 and 36, respectively. Compound 35 and 36 were converted to the corresponding phosphoramidites, Compound 37 and 38, respectively, by treatment with 2-cyanoethyl-N, N-diisopropylchlorophosphor-amidite.

Reactions of Compound 29 with Grignard reagents afford 4'-C-alkylthymidines and 4'-C-alkenylthymidines. Hydroboration or oxidative cleavage of the resulting 4'-C-(w-alkenyl) thymidines yields hydroxyalkylthymidines, hydroxyl of which can be converted to a variety of functionalities such as $NH_2$, OR, SR, SH, and X, where R is H, or alkyl, and X is F, Cl, Br, I, or OTs. Reactions of Compound 29 with caynoalkylcadmium afford 4'-C-cyanoalkylthymidines. Reactions of Compound 29 with ethoxycarbonylalkylzinc reagents afford 4'-C-ethoxycarbonylalkylthymidines, which can be hydrolyzed to 4'-C-carboxyalkylthymidines. Reactions of Compound 29 with sodium alkoxides afford 4'-C-alkoxymethylthymidines. Substituted alcohols and phenols can be used to prepare 4'-C-substituted alkoxymethylthymidines. The substituents may be $NO_2$, CN, COOEt, OAc or protected amino groups. After the 4'-C-branched thymidines are synthesized, 5'-hydroxyl groups are protected with dimethoxytrityl and 3'-hydroxyl groups are converted to phosphoramidite for oligonucleotide synthesis by a standard procedure (F. Eckstein, "Oligonucleotide synthesis", Oxford University Press (1991)).

Synthesis of 5'-C-branched Nucleosides

Figure 8:
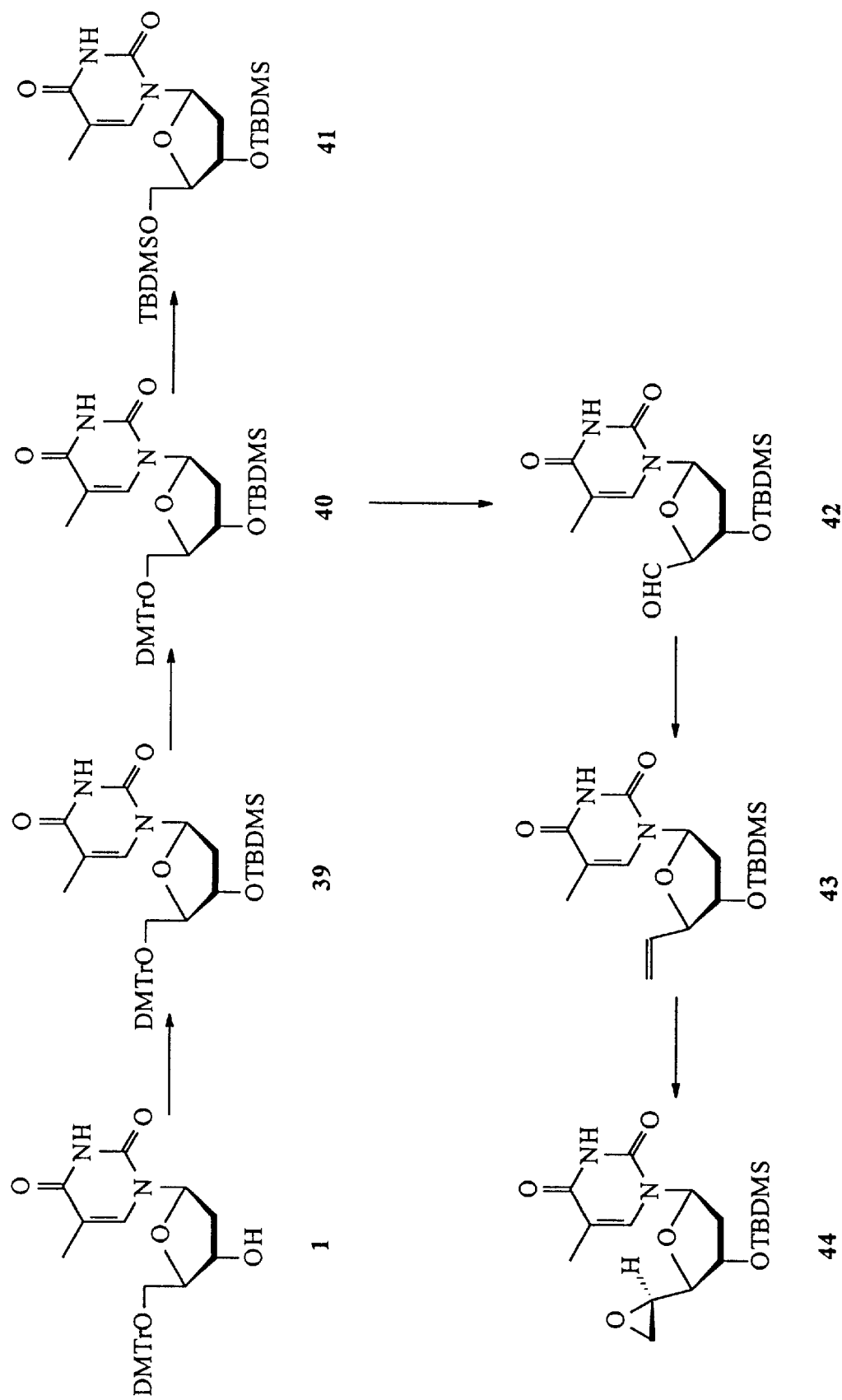
FIG. 8 shows reaction scheme 6, for the synthesis of 5'-C-branched thymidine.
Figure 9:
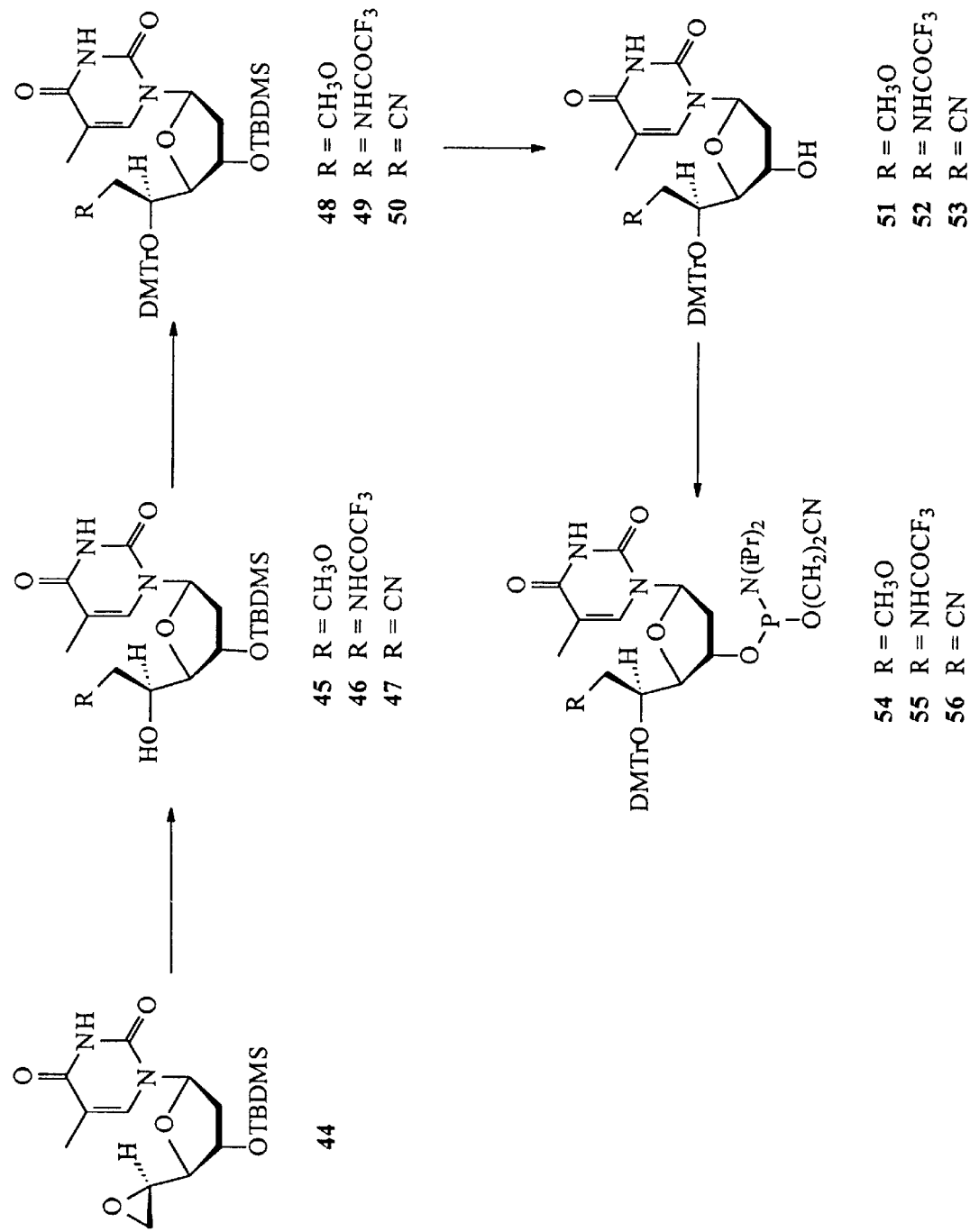
FIG. 9 shows additional aspects of reaction scheme 6, for the synthesis of 5'-C-branched thymidine.
Figure 10:
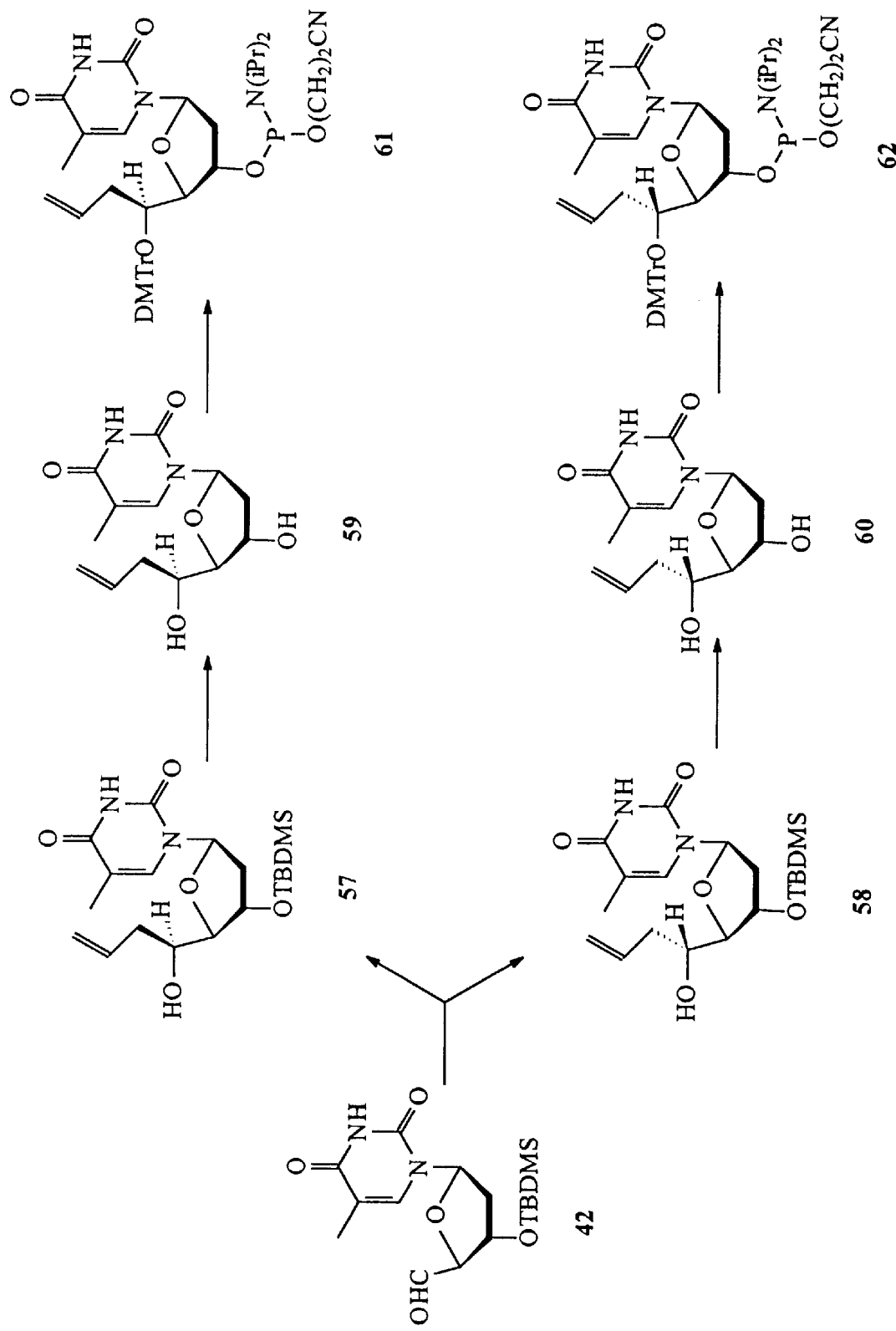
FIG. 10 shows reaction scheme 7, for the synthesis of 5'-C-branched thymidine.
Figure 12:
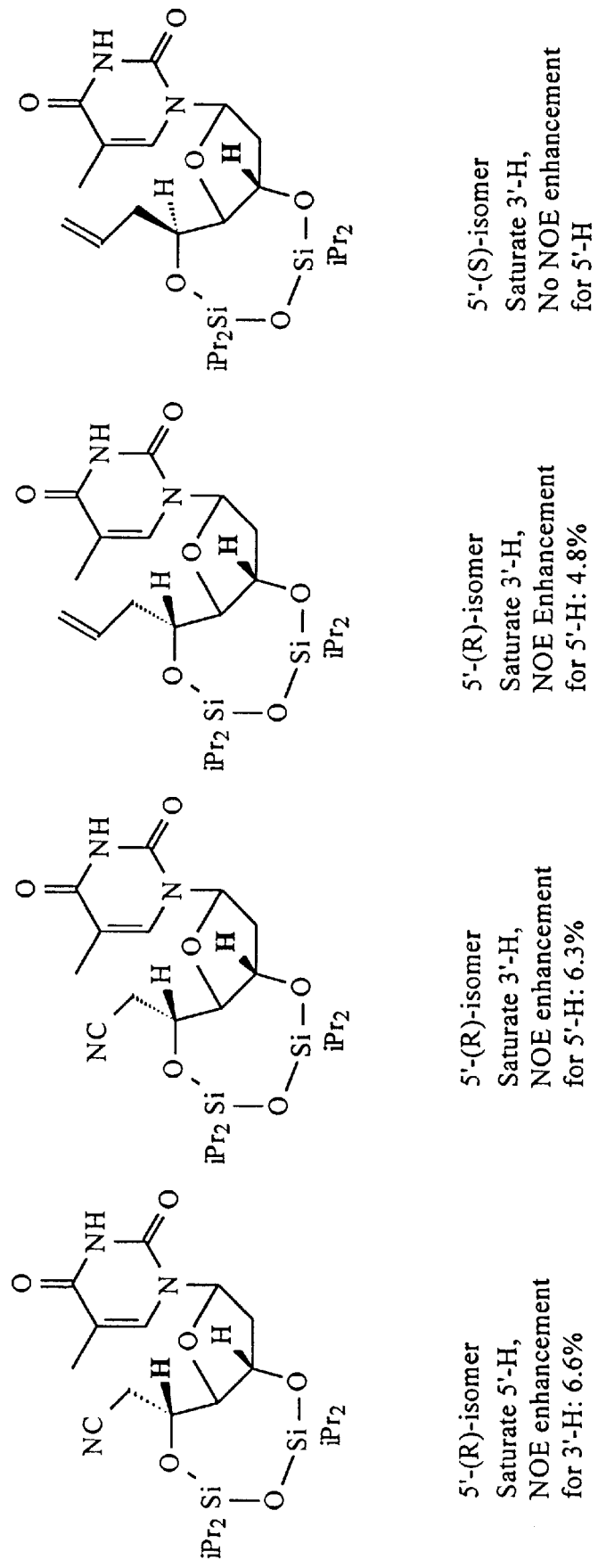
FIG. 12 is chart showing stereochemistry assignments of Compound 44 and others.

This invention provides procedures for preparation of a large number of 5'-C- branched nucleosides. Examples of methods of preparing 5'-C-branched thymidines are shown in Reaction schemes 6, 7, and 8 (FIGS. 8, 9, and 10, respectively). These procedures may be readily adapted for the synthesis of other nucleosides of the invention, including embodiments of the invention in which the nucleosides comprise a base other than thymine. Compound 42 was prepared in three steps by a known procedure (O-Yang C., Wu, H. Y., Fraser-Smith, E. B., Walker, K. A. M. *Tetrahedron Letts.* 1992, 33, 37–40). Alternatively, Compound 42 was prepared from reaction of 80% acetic acid with Compound 41, 3', 5'-O-(bis-t-butyldimethyl-silyl)thymidine prepared from reaction of thymidine with excess t-butyldimethylchlorosilane and imidazole in pyridine. Wittig Reaction of Compound 42 and phosphorus ylide, prepared from methyltriphenylphosphonium bromide and sodium hydride in DMSO, afforded an olefinic derivative, Compound 43. Epoxidation of Compound 43 with m-chloroperoxybenzoic acid in dichloromethane afforded a 5'-(S)-epoxide derivative, Compound 44 as the major product and a 5'-(R)-epoxide derivative as minor product. Stereochemistry assignments of Compound 44 and others are shown in Chart 1 (FIG. 12). Reaction of Compound 44 with methanol in the presence of sodium carbonate afforded 5'-(S)-C-methoxymethylthymidine, Compound 45. Reaction of Compound 44 with ammonia in methanol afforded 5'-(S)-C-amino-methylthymidine, which was protected with trifluoroacetyl to give Compound 46. Reaction of Compound 44 with potassium cyanide in DMF afforded 5'-(S)-C-cyanomethylthymidine, Compound 47. 5'-hydroxyl groups of Compounds 45–47 were protected with dimethoxytrityl by reactions with dimethoxytrityl chloride and silver trifluoromethanesulfonate in pyridine to give Compounds 48–50, respectively. TBDMS groups of Compounds 48–50 were removed with TBAF in THF to give Compounds 51–53, respectively. Compounds 51–53 were converted to the corresponding phosphoramidites, Compounds 54–56, respectively. Grignard reaction of Compound 42 with allylmagnesium bromide yielded a mixture of isomeric 5'-(R)-C-ailylthymidine and 5'-(S)-C-allylthymidine derivatives, Compounds 57 and 58, which are separated by chromatography on silica. TBDMS groups of Compound 57 and 58 were removed by treatment with TBAF in THF to give 5'—(R)— and 5'-(S)—-C-allylthymidines, Compound 59 and 60 , respectively. Compound 59 and 60 were converted to the corresponding phosphoramidites, Compound 61 and 62, respectively. Similarly, reactions of Compound 42 with a variety of Grignard Reagents afford a variety of 5'-(S or R)-C-alkylthymidines and 5'-(S or R)-C-alkenylthymidines. Hydroboration or oxidative cleavage of the resulting 5'-C-(ω-alkenyl)thymidines yields hydroxyalkylthymidines, hydroxyl of which can be converted to a variety of functionalities such as $NH_2$, OR, SR, SH, and X, where R is H, or alkyl, and X is F, Cl, Br, I, Ots.

Figure 11:
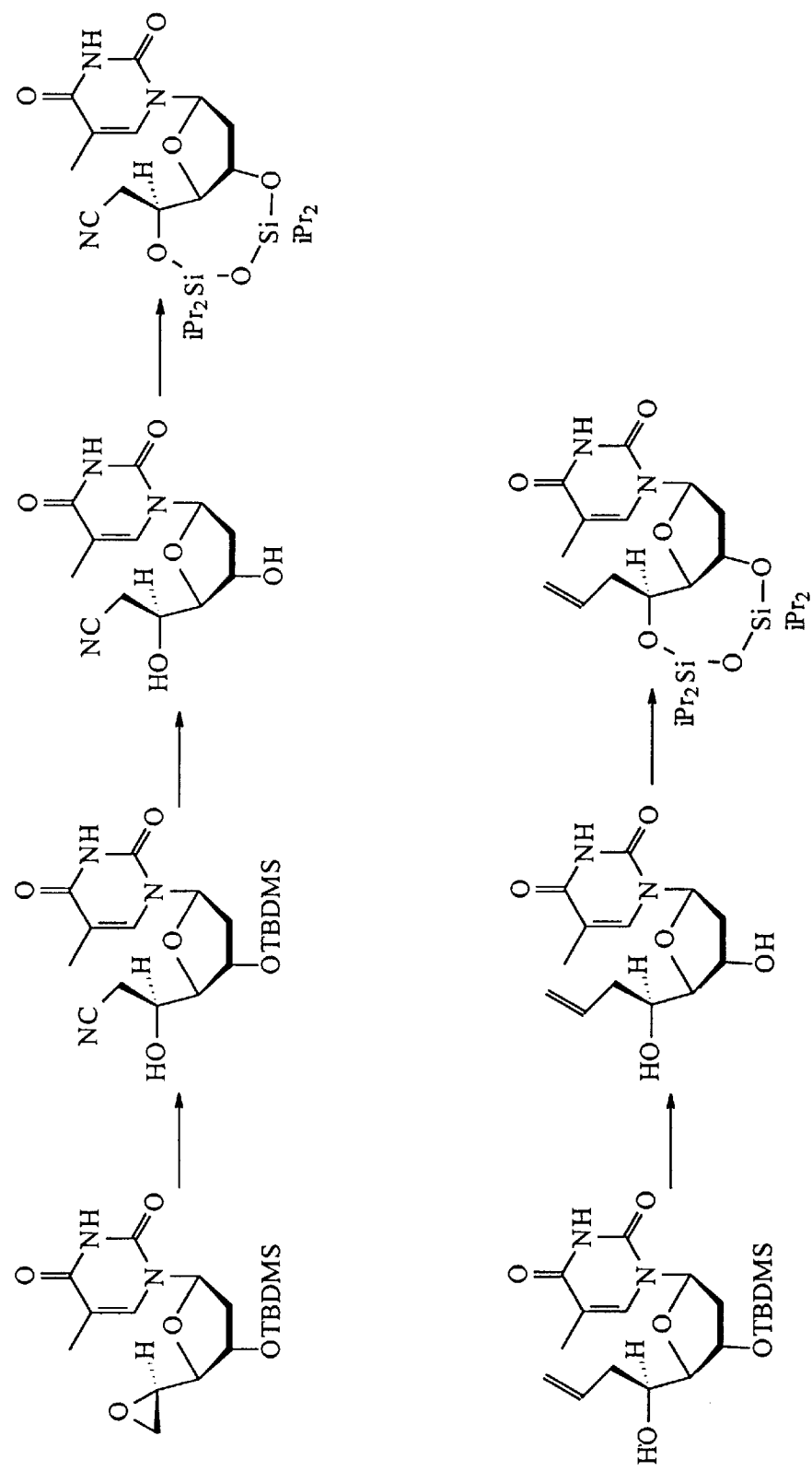
FIG. 11 shows reaction scheme 8, for the synthesis of 5'-C-branched thymidine.

Reactions of Compound 44 with a variety of nucleophilic reagents can afford a wide variety of 5'-C-branched thymidine derivatives. Thus, reactions of Compound 44 with alcohols in the presence of a base give 5'-C-alkoxymethylthymidines. Substituted alcohols can also be used to prepare 5'-C-substituted alkoxymethylthymidines. The substituents may include, but not limited to, $NO_2$, CN, COOEt, and protected amino groups. Reaction of Compound 44 with diols affords 5'-C-hydoxyalkoxymethylthymidines, which can be readily converted to 5'-C-haloalkylthymidines. Reaction of Compound 44 with nitromethane gives 5'-C-nitroethyl thymidine. Reduction of 5'-C-nitroalkylthymidines affords 5'-C-aminoalkyl-thymidines. Reaction of Compound 44 with cyanoalkylcadmium reagents gives 5'-C-cyanoalkyl thymidines. Reaction of Compound 44 with ethoxycarbonylalkylzinc reagents affords 5'-C-ethoxycarbonylalkylthymidines, which are readily hydrolyzed to 5'-C-carboxyalkylthymidines at basic condition. All the transformations of 5'-(S)-isomers are equally applied to 5'-(R)-isomers. Finally, reactions of 5'-C-branched thymidines with dimethoxytrityl chloride and silver triflate in pyridine to yield 5'-O-DMTr-5'-C-branched thymidines, which are converted to the corresponding phosphoramidites, respectively by a standard procedure (F. Eckstein, "Oligonucleotide synthesis", Oxford University Press (1991)) For determining configurations at C5' positions of 5'-C-branched thymidines the advantage of NOE enhancement of spatially closed protons was utilized. Since rigid orientations of the substituents at C5' are essential for NOE experiments, a TIPDS-ring between 3'-O- and 5'-O- of the thymidine derivatives was introduced (Scheme 8, FIG. 11), where 5'-protons orient either towards 3'-protons or away from 3'-protons. When 3'-protons are saturated, presence or absence of NOE enhancement of 5'-protons can be readily observed (Chart 1, FIG. 12). For 5'-C-allylthymidines the isomer that has 4.8% NOE enhancement is clearly the 5'-(R)-isomer and the other that has no NOE enhancement the 5'-(S)-isomer. Without X-ray crystallography direct determination of stereochemistry of 5'-epoxy group is a challenge. However, conversion of the epoxides to the ring-opening products does not alter chirality at C5'. If stereochemistry of one pair of such ring-opening products is determined, stereochemistry of the epoxide pair is also assigned. Thus, similarly to 5'-C-allylthymidines, a pair of ring-opening products, 5'-C-cyanomethylthymidines prepared from the epoxides, were converted to TIPDS-ring products. When 3'-protons were saturated, one isomer gave 6.3% NOE enhancement. Clearly, this isomer is 5'-(R)-isomer and the other 5'-(S)-isomer.

Synthesis of 1'-C-branched Nucleosides

Figure 13:
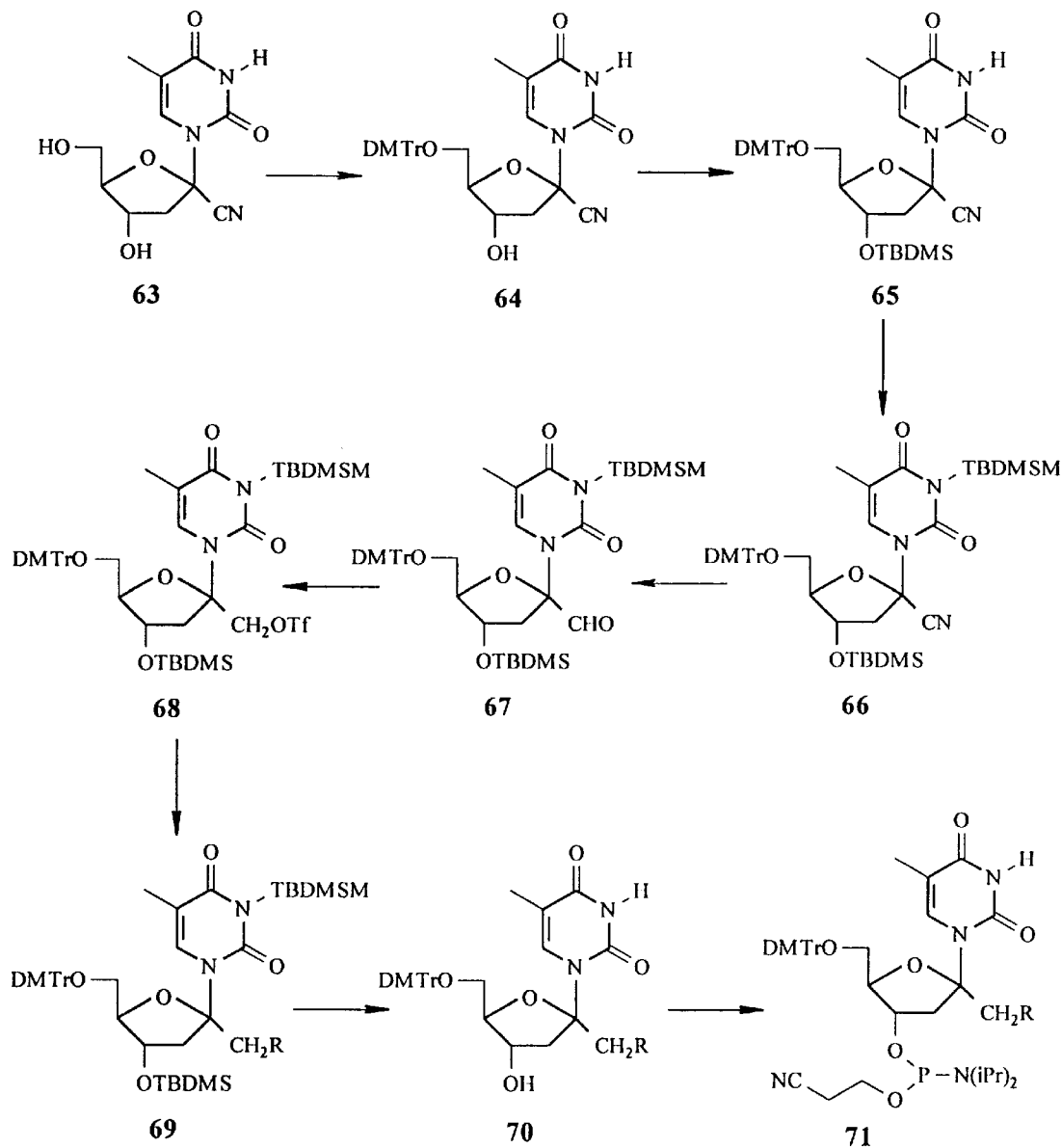
FIG. 13 shows reaction scheme 9, for the synthesis of 1'-C-branched thymidine.
Figure 14:
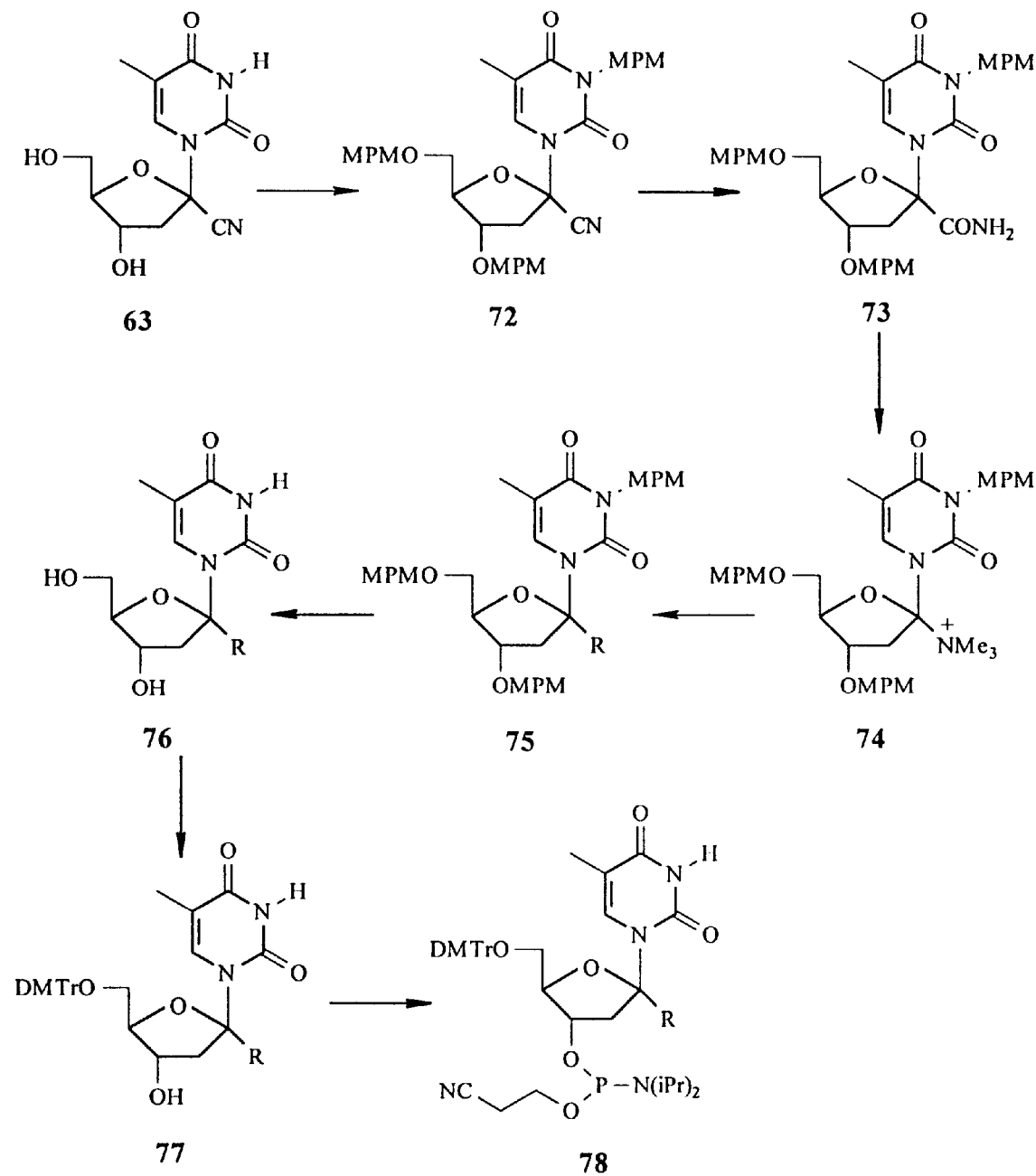
FIG. 14 shows reaction scheme 10 for the synthesis of 1'-C-branched thymidine.

Several 1'-C-branched nucleosides have been reported (a. Uteza, V., Chen, G-R., Tuoi, J. L. Q., Descotes, G., Fenet, B., Grouiller, A. *Tetrahedron*, 1993, 49, 8579–8588; B. Azhayev, A., Gouzaev, A., Hovinen, J., Azhayeva, E., Lonnberg, H. *Tetrahedron Letts.* 1993, 34, 6435–6438). This invention provides procedures for preparation of a large number of 1'-C-branched nucleosides. Preparation of 1'-C-branched thymidines is shown in Reaction schemes 9 and 10 (FIGS. 13 and 14, respectively). Compound 63 is prepared according to a known procedure (Uteza, V., Chen, G-R., Tuoi, J. L. Q., Descotes, G., Fenet, B., Grouiller, A. *Tetrahedron*, 1993, 49, 8579–8588). 5'-Hydroxyl group of Compound 63 is protected by dimethoxytrityl to give Compound 64, which is treated with t-butyldimethylchlorosilane affords Compound 65. Treatment of Compound 65 with t-butyldimethylsiloxymethyl chloride affords Compound 66. Treatment of Compound 66 with lithium triethoxyaluminum hydride in ether affords an aldehyde, Compound 67. Reduction of Compound 67 with sodium borohydride, followed by treatment with trifluoromethanesulfonic anhydride, affords a triflate derivative, Compound 68. Treatment of Compound 68 with a wide variety of nucleophilic reagents affords a number of new 1'-C-branched thymidines, Compounds 69. Thus, treatment of Compound 68 with sodium cyanide, nitrite, azide affords the corresponding 1'-C-cyanomethyl, 1'-C-nitromethyl, and 1'-C-azidomethylthymidines, respectively. Treatment of Compound 68 with nitromethane affords 1'-C-nitroethyl thymidine. Treatment of Compound 68 with sodium alkyl sulfides affords 1'-C-alkylthiomethylthymidine. Treatment of Compound 68 with sodium alkoxide affords 1'-C-alkoxymethylthymidine. Treatment of Compound 68 with lithium organocuprate reagents affords 1'-C-alkyl- and 1'-C-alkenylthymidines. Substituted alkyl or alkenylzinc or cadmium reagents can be used to prepare 1'-C-substituted alkyl or 1'-C-substituted alkenylthymidines. The substituents may be COOEt, CN, $NO_2$. Hydroboration or oxidative cleavage of the resulting 3'-C-(ω-alkenyl)thymidines yields hydroxyalkylthymidines, hydroxyl of which can be converted to a variety of functionalities such as $NH_2$, OR, SR, SH, and X, where R is H, or alkyl, and X is F, Cl, Br, I, OTs. Substituted alcohols and phenols can be used to prepare 1'-C-alkoxymethyl- and 1'-C-phenoxymethylthymidines. The substituents may be $NO_2$, CN, COOEt, or OAc. 1'-C-Nitroalkylthymidines can be reduced to the corresponding aminoalkylthymidines. Compounds 69 are treated with TBAF to give deprotected Compounds 70, which are converted to the corresponding phosphoramidites, Compounds 71.

Compound 63 is fully protected with p-methoxybenzyl (MPM) group to give Compound 72. Hydrolysis of Compound 72 in the presence of hydrogen peroxide and base affords Compound 73, which is subjected to Hofmann rearrangement to afford an amine that can be converted with methyl bromide to a quarternary ammonium derivative, Compound 74. A variety of nucleophiles can be used to replace trimethylamine. Treatment of Compound 74 with sodium alkoxide affords 1'-C-alkoxythymidines. Treatment of Compound 74 with sodium alkyl sulfide affords 1'-C-alkylthiothymidines. When heated with sodium bromide, Compound 74 can be converted to 1'-C-bromothymidine, which is treated with sodium azide, sodium nitrite, or boromethane to give the corresponding 1'-C-substituted thymidines, respectively. Compounds 75 are treated with cerium ammonium nitrate to give deprotected Compounds 76. 5'-Hydroxyl is protected with dimethoxytrityl and the resulting products, Compounds 77, are converted to the corresponding phosphoramidites, compounds 78.

Oliaonucleotides containing the Sugar Modified Nucleosides

Oligonucleotides containing sugar-modified nucleosides has been reported recently (A. Jorgensen, P. N., Stein, P. C., Wengel, J. *J. Am. Chem. Soc.* 1994, 116, 2231; B. Fensholdt, J., Thrane, H., Wengel, J. *Tetrahedron Letts.* 1995, 36, 2535; C. Thrane, H., Fensholdt, J., Regner, M., Wengel, J. *Tetrahedron*, 1995, 51, 10389; D. Saha, A. K., Caulfield, T. J., Hobbs, C., Upson, D. A., Waychunas, C., Yawman, A. M. *J. Org. Chem.* 1995, 60, 788; E. Azhayev, A., Gouzaev, A., Hovinen, J., Azhayeva, E., Lonnberg, H. *Tetrahedron Lett.* 1993, 34, 6435–6438; F. Ono, A., Dan, A., Matsuda, A. *Bioconjugate Chemistry*, 1993, 4, 499–508; G. Inoue, H., Hayase, Y., Imura, A., Iwai, S., Miuta, K., Ohtsuka, E., *Nucleic Acids Res.* 1987, 15, 6131; H. Lesnik, E. A., Guinosso, C. J., Kawasaki, A. M., Sasmor, H., Zounes, M., Cummins, L. L., Ecker D. J., Cook, P. D., and Freier, S. M. *Biochemistry*, 1993,32, 7832) This invention provides a large number of novel, sugar-modified nucleosides that can be readily incorporated into oligonucleotides by phosphoramidite chemistry. The sugar-modified oligonucleotides contain at least one of the sugar modified nucleosides of the invention, they may contain multiple sugar-modified nucleosides in a sequence, or they may contain only the sugar-modified nucleosides of the invention. The sugar-modified oligonucleotides may also contain other modifications such as backbone modifications, base modifications, and any other sugar modifications. It is apparent that branched substituents at C3' or C5' of the nucleosides would reduce the coupling rate, depending on the size of the substituents. Therefore, for some bulky substituent branched nucleosides, coupling time have been increased. Thus, for synthesis of 5'-C-branched oligonucleotides and 4'-C-branched oligonucleotides a coupling time of 2–5 minutes have been used. For synthesis of 3'-C-branched oligonucleotides a coupling time up to 45 minutes (3×15 min) has been used. Repeated couplings with fresh reagents are necessary only for synthesis of 3'-C-branched oligonucleotides since 3'-hydroxyl is tertiary. Composition of purified sugar-modified oligonucleotides are verified by analysis of enzyme digestion products.

EXAMPLES

The invention having been described above, may be better understood by reference to the following examples. The following examples are intended to illustrate but not to limit the invention.

Example 1

Preparation of 5'-O-(4,4'-dimethoxytrityl)-3'-p-tosyloxymethylthymidine

A solution of 5'-O-(4,4'-dimethoxytrityl)-3'- hydroxymethylthymidine (2.12 g, 3.69 mmol), prepared according to a known procedure (Jorgensen, P. N., Thrane, H., Wengel, J. *J. Am. Chem. Soc.* 1994, 116, 2231), p-toluenesulfonyl chloride (1.76 g, 9.23 mmol), DMAP (0.180 g, 1.48 mmol) in anhydrous pyridine (13 ml) was stirred at room temperature overnight. The reaction mixture was cooled to 0° C., diluted with EtOAc (500 ml), washed with 10% NaHCO$_3$, dried over Na$_2$SO$_4$, and concentrated. The crude was purified by chromatography on silica (5% CH$_3$OH in CH$_2$Cl$_2$) to yield 2.39 g (89%) of 5'-O-(4,4'-dimethoxytrityl)-3'-p-tosyloxymethylthymidine as a colorless powder.

Example 2

Preparation of 5'-O-(4,4'-dimethoxytrityl)-3'-C-cyanomethylthymidine

A slurry of 5'-O-(4,4'-dimethoxytrityl)-3'-p-toluensulfonyloxymethylthymidine (0.50 g; 0.686 mmol) and potassium cyanide (0.134 g; 2.06 mmol) in anhydrous DMF (7 ml) was stirred at room temperature overnight. The reaction mixture was diluted with EtOAc (60 ml) and washed with water (3×75 ml), then with 10% NaHCO$_3$ (3×75 ml). The organic layer was dried over Na$_2$SO$_4$, concentrated, and purified by chromatography on silica (EtOAc-Hexanes, 1:1) to yield 0.386 g (97%) of 5'-O-(4,4'-dimethoxytrityl)-3'-C-cyanomethylthymidine as a colorless powder.

Example 3

Preparation of 5'-O-(4,4'-dimethoxytrityl)-3'-C-azidomethylthymidine

A slurry of 5'-O-(4,4'-dimethoxytrityl)-3'-p-toluensulfonyloxymethylthymidine (0.40 g; 0.55 mmol) and NaN$_3$ (0.11 g; 1.65 mmol) in anhydrous DMF (3 ml) was heated at 50° C. for 3 days. The reaction mixture was cooled to room temperature, diluted with EtOAc (30 ml), and washed with water (3×40 ml), then with 10% NaHCO$_3$ (3×40 ml). The organic layer was dried over Na$_2$SO$_4$, concentrated and purified by chromatography on silica (EtOAc-Hexanes, 1:1) to yield 0.30 g (92%) of 5'-O-(4,4'-dimethoxytrityl)-3'-C-azidomethylthymidine as a colorless powder.

Example 4

Preparation of 5'-O-(4,4'-dimethoxytrityl)-3'-C-cyanomethylthymidine 3'-(2-cyanoethyl-N,N-diisopropylphosphoramidite)

To a stirred solution of 5'-O-(4,4'-dimethoxytrityl)-3'-C-cyanomethylthymidine (0.20 g; 0.344 mmol) and diisopropylethylamine (0.24 ml; 1.38 mmol) in anhydrous dichloromethane (3 ml) at 0° C. under argon was added dropwise a solution of 2'-cyanoethyl-N,N-diisopropylchlorophosphoramidite (170 mg; 0.715 mmol) in dichloromethane. The resulting reaction mixture was stirred at room temperature for 2 h, cooled to 0° C., diluted with cold CH$_2$Cl$_2$ (20 ml), and washed with cold NaHCO$_3$ (3×15 ml). The organic layer was dried over Na$_2$SO$_4$, concentrated. The residue was purified by chromatography on silica (Et$_3$N— EtOAc— CH$_2$Cl$_2$, 5:50:45) to yield 177 mg (66%) of 5'-O (4,4'-dimethoxytrityl)-3'-C-cyanomethylthymidine 3'-(2-cyanoethyl-N,N-diisopropyl-phosphoramidite) as a foam.

Example 5

Preparation of 5'-O-(4,4'-dimethoxytrityl)-3'-C-azidomethylthymidine 3'-(2-cyanoethyl-N,N-diisopropylphosphoramidite)

To a stirred solution of 5'-O-(4,4'-dimethoxytrityl)-3'-C-azidomethylthymidine (252 mg; 0.344 mmol) and diisopropylethylamine (0.44 ml; 2.51 mmol) in anhydrous dichloromethane (3 ml) at 0° C. under argon was added dropwise a solution of 2'-cyanoethyl-N,N-diisopropylchlorophosphoramidite (296 mg; 1.25 mmol) in dichloromethane. The resulting reaction mixture was stirred at room temperature for 2 h, cooled to 0° C., diluted with cold CH$_2$Cl$_2$ (20 ml), and washed with cold NaHCO$_3$ (3×15 ml) The organic layer was dried over Na$_2$SO$_4$, concentrated. The residue was purified by chromatography on silica (Et$_3$N—EtOAc—CH$_2$Cl$_2$, 5:50:45) to yield 128 mg (38%) of 5'-O (4,4'-dimethoxytrityl)-3'-C- azidomethylthymidine 3'-(2-azidomethyl-N, N-diisopropyl-phosphoramido) as a foam.

Example 6

Preparation of 5'-O-(4,4'-dimethoxytrityl)-3'-C,O-methylenethymidine

To a suspension of NaH (60% in mineral oil, 0.18 g; 7.5 mmol) in anhydrous THF (18 ml) at 0° C. under argon was added dropwise a solution of 5'-O-(4,4'-dimethoxytrityl)-3'-p-toluensulfonyloxymethylthymidine (1.5 g; 2.06 mmol) in THF (10 ml). The resulting reaction mixture was stirred at room temperature for 2 h, cooled to 0° C., and quenched by addition of water. The mixture was diluted with EtOAc (250 ml), washed with water (2×200 ml), then with 10% NaHCO$_3$ (2×200 ml), dried over Na$_2$SO$_4$, and concentrated. The residue was purified by chromatography on silica (5% CH$_3$OH in CH$_2$Cl$_2$) to yield 0.97 g (85%) of 5'-O-(4,4'-dimethoxytrityl)-3'-C,O-methylene thymidine as a foam.

Example 7

Preparation of 5'-O-(4,4'-dimethoxytrityl)-3'-C-methylthymidine

To a stirred, suspension of lithium aluminum hydride (58 mg; 1.53 mmol) in anhydrous THF (10 ml) at 0° C. under argon was added dropwise a solution of 5'-O-(4,4'-dimethoxytrityl)-3'-C,O-methylenethymidine (385 mg; 0.692 mmol) in THF (10 ml). The reaction mixture was stirred at 0° C. for 1 h and the reaction quenched by slow addition of 10% NaHCO$_3$, The resulting mixture was diluted with EtOAc (30 ml), washed with NaHCO$_3$ (3×20 ml, dried over Na$_2$SO$_4$, and concentrated. The residue was purified by chromatography on silica (5% CH$_3$OH in CHCl$_3$) to yield 306 mg (79%) of 5'-O-(4,4'-dimethoxytrityl)-3'-C-methylthymidine as a foam.

Example 8

Preparation of 5'-O-(4,4'-dimethoxytrityl)-3'-C-methylthymidine 3'-(2-cyanoethyl-N N-diisopropyphosphoramidite)

To a stirred solution of 5'-O-(4,4'-dimethoxytrityl)-3'-C-methylthymidine (98 mg, 0.17 mmol) and diisopropylethylamine (0.13 ml, 0.742 mmol) in anhydrous dichloromethane (2 ml) at 0° C. under argon was added dropwise a solution of 2'-cyanoethyl-N,N-diisopropylchlorophosphoramidite (85 mg, 0.36 mmol) in dichloromethane. The resulting reaction mixture was stirred at room temperature for 1 h, cooled to 0° C., diluted with cold CH$_2$Cl$_2$ (20 ml), and washed with cold NaHCO$_3$ (3×15 ml). The organic layer was dried over Na$_2$SO$_4$, concentrated. The residue was purified by chromatography on silica (Et$_3$N- EtOAc-hexane, 5:50:45) to yield 117 mg (88%) of 5'-O (4,4'-dimethoxytrityl)-3'-C-methylthymidine 3'-(2-cyanoethyl-N,N-diisopropylphosphoramidite) as a foam.

Example 9

Preparation of 5'-(4,4'-dimethoxytrityl)-3'-C-aminomethylthymidine

A saturated solution of ammonia in methanol (9 ml) was added to a solution of 5'-O-(4,4'-dimethoxytrityl)-3'-C,O-methylenethymidine (901 mg; 1.62 mmol) in methanol (3 ml), and the resulting solution stood at room temperature for 3 days. Excess ammonia and methanol was evaporated and the residue purified by chromatography (CH,OH- Hexanes-CHC13, 1:1:8) to yield 414 mg (45%) of 5'-O-(4,4'-dimethoxytrityl)-3'-C-aminomethylthymidine as a colorless solid.

Example 10

Preparation of 5'-O-(4,4'-dimethoxytrityl)-3'-C-trifluoroacetamidomethylthymidine A solution of 5'-O-(4,4'-dimethoxytrityl)-3'-C-aminomethylthymidine (361 mg; 0.628 mmol) and ethyl thiotrifluoroacetate (490 mg, 3.12 mmol) in anhydrous THF (6 ml) was stirred at room temperature for 6 h. Solvent was evaporated and the residue purified by chromatography on silica (5% CH$_3$OH in CH$_2$Cl$_2$) to yield 411 mg (98%) of 5'-O-(4,4'-dimethoxytrityl)-3'-C-trifluoroacetamidomethylthymi dine as a colorless powder.

Example 11

Preparation of 5'-O-(4,4'-dimethoxytrityl)-3'-C-trifluoroacetamidomethyl-thymidine 3'-(2-cyanoethyl-N,N-diisopropylphosphoramidite)

To a stirred solution of 5'-O-(4,4'-dimethoxytrityl)-3'-C-methylthymidine (411 mg, 0.614 mmol) and diisopropyl-ethylamine (0.64 ml, 3.65 mmol) in anhydrous dichloromethane 2'-cyanoethyl-N-, N-diisopropylchlorophosphoramidite (410 mg, 1.83 mmol) in anhydrous dichloromethane. The resulting reaction mixture was stirred at room temperature for 2 h, cooled to 0° C., diluted with cold CH$_2$Cl$_2$ (30 ml), and washed with cold NaHCO$_3$ (3×20 ml). The organic layer was dried over Na$_2$SO$_4$ and concentrated. The residue was purified by

Example 12

Preparation of 3'-O-(4,4'-dimethoxytrityl)-5'-formylthymidine

To a stirred, cold solution of 3'-O-(4,4'-dimethoxy-trityl) thymidine (prepared from thymidine by the common procedures, 40.4 g, 0.072 mol) in anhydrous DMSO was added a solution of DCC (45.86 g, 0.224 mol) in DMSO (180 ml). The resulting solution was stirred at 5° C. for 5 min. pyridine (2.94 g, 3.0 ml, 0.0371 mol) was added and after stirring for another 5 min. a solution of trifluorocaetic acid (2.11 g, 1.43 ml, 0,0185 mol) in DMSO (2 ml) was added dropwise. The resulting reaction mixture was stirred at 5° C. for 10 min. and at room temperature for 6 h. Water (20 ml) was added dropwise under cooling and the mixture stirred at room temperature for 1 h. Precipitates were filtered and washed with DMSO. The combined DMSO solution was poured onto crashed ice (4 L) with stirring. After standing for 1 h, the precipitates were filtered and washed thoroughly with water. The cake was dissolved in methylene chloride (5 00 ml), and the organic layer separated, dried (Na$_2$SO$_4$), and concentrated. The crude was purified by chromatography on silica (3% methanol in methylene chloride) to give 32.6 g (81%) of 3'-O-(4,4'di-methoxytrityl)-5'-formylthymidine as a colorless powder.

Example 13

Preparation of 3'-O-(4,4'-dimethoxytrityl)-4'-C-hydroxymethylthymidine

To a stirred solution of 3'-O-(4,4'dimethoxytrityl)-5'-formylthymidine (16.3 g, 30.07 mmol) in dioxan (120 ml) at 0° C. was added dropwise, in turn, 36% formaldehyde (24 ml) and 2N NaOH (60 ml). The resulting solution was stirred at room temperature for 6 h. The reaction mixture was cooled to 0° C. and 10% acetic acid in water added dropwise until pH reached 7.5. The mixture was diluted with ethyl acetate (1 L), washed with 10% brine (500 ml, then 2×300 ml), dried (Na$_2$SO$_4$), and concentrated. The crude was purified by chromatography on silica (EtOAc-hexane, 3:1) to give 11.45 g (66.3%) of 3'-O-(4,4'-dimethoxytrityl)-4'-C-hydroxymethylthymidine as a colorless powder.

Example 14

Preparation of 4'-C-hydroxymethylthymidine

A solution of 3'-O-(4,4'-dimethoxytrityl)-4'-C-hydroxymethylthymidine (6.32 g, 11.o mmol) in 80% acetic acid in water (50 ml) stood at room temperature fro 4 h. Solvents were removed under reduced pressure and water (200 ml) added. The resulting cloudy mixture was washed with ether (3×80 ml) and water was evaporated. The residue was dissolved in methanol and toluene and the resulting solution was concentrated. This process was repeated twice. 4'-C-hydroxymethylthymidine (2.72 g, 91%) was obtained as a foam.

Example 15

Preparation of 4'-C-benzoyloxymethylthymidine

To a stirred solution of 4'-hydroxyxmethylthymidine (3.72 g, 13.67 mmol) in anhydrous pyridine (10 ml) at 0° C. was added a solution of benzoic anhydride (4.64 g, 51 mmol) in pyridine (10 ml). The resulting solution stood at 0° C. for 1 h and then at room temperature for 20 h. Water (5 ml) was added at 0° C., pyridine was evaporated, and the residue chromatographed on silica (7% ethanol in chloroform) to give 2.27 g (44%) of 4'-C-benzoyloxymethylthymidine as a colorless solid.

Example 16

Preparation of 3,5'-O-(bis-tetrahydropyranyl)-4'-C-hydroxymethylthymidine

To a stirred solution of 4'-C-benzoyloxymethylthymidine (1.65 g, 4.39 mmol) and p-toluenesulfonic acid (50 mg) ) in anhydrous methylene chloride (70 ml) at 0° C. was added dropwise dihydropyran (1.84 g, 1.89 ml, 21.80 mmol). The resulting solution was stirred at room temperature for 2 h. 2N NaOH (20 ml) was added under cooling, the resulting mixture concentrated to remove methylene chloride, and dioxane (10 ml) added. The mixture was stirred at room temperature for 3 h and extracted with methylene chloride (3×30 ml). The organic layer was washed with water (3×50 ml), dried (Na$_2$SO$_4$), and concentrated. The residue was purified by filtration through a silica column to give 1.50 (77.7%) of 3', 5'-O-(bis-tetrahydropyranyl)-4'-C-hydroxymethylthymidine as a foam.

Example 17

Preparation of 4'-C-methoxymethylthymidine

To a stirred mixture of 3', 5'-O-(bis-tetrahydropyranyl)-4'-C-hydroxymethylthymidine (660 mg, 1.5 mmol) and sodium hydride (60% in mineral oil, 10 mg, 4.5 mmol) in anhydrous THF (15 ml) at 0° C. was added methyl iodide dropwise (1.06 g, 0.46 ml). The resulting mixture was stirred at 0° C. for 1.5 h. Water (1 ml) was added dropwise at 0° C. and acetic acid added to adjust PH to 7. The mixture was diluted with ethyl acetate (50 ml), washed with water (3×30 ml), dried (Na$_2$SO$_4$), and concentrated. The residue was dissolved in an acidic mixture (5 ml THF, 10 ml CH$_3$COOH, and 5 ml water), the solution stood at 50° C. for 3 h, and solvents were evaporated. The residue was dissolved in methanol-toluene mixture, concentrated, and repeated once. Purification by chromatography on silica (10% ethanol in chloroform) yielded 271 mg (63%) of 4'-C-methoxymethylthymidine as a colorless solid.

Example 18

Preparation of 5'-O-(4,4'-dimethoxytrityl)-4'-C-methoxymethylthymidine

A solution of 4'-C-methoxymethylthymidine (173 mg, 0.6 mmol) and dimethoxytrityl chloride (287 mg, 0.84 mmol) in pyridine stood at room temperature for 5 h. Pyridine was evaporated and the residue purified by chromatography on silica (EtOAc-hexane, 2:1) to give 264 mg (74%) of 5'-O-(4,4'-dimethoxytrityl)- 4'-C-methoxymethylthymidine as a foam.

Example 19

Preparation of 5'-O-(4,4'-dimethoxytrityl)-4'-C-methoxvmethylthymidine 3'-(2-cyanoethyl-N,N-diisopropylphosphoramidite)

To a stirred solution of 5'-O-(4,4'-dimethoxytrityl)-4'-C-methoxymethylthymidine (200 mg, 0.34 mmol) and diisopropylethylamine (176 mg, 236 µl, 1.36 mmol) in anhydrous methylene chloride (3 ml) at 0° C. under nitrogen was added dropwise a solution of 2-cyanoethyl-N,N-diisopropyl-chlorophosphoramidite (161 mg, 152 µl, 0.68 mmol) in methylene chloride (1 ml). The resulting solution was stirred at room temperature for 30 min., cooled to 0° C., and diluted with ethyl acetate (30 ml). The mixture was washed with 10% NaHCO$_3$ (3×20 ml), dried (Na$_2$SO$_4$), and concentrated. The residue was purified by chromatography on silica (Et$_3$N-EtOAc-hexane, 5:45:50) to give 190 mg (71%) of 5'-O-(4,4'-dimethoxytrityl)-4'-C-methoxymethylthymidine 3'-(2-cyanoehthyl-N, N-diisopropyl-phosphoramidite) as a foam.

Example 20

Preparation of 3', 5'-(bis-t-butyldimethylsilyl)-4'-C-hydroxymethylthymidine

To a cold, stirred solution of 4'-C-benzoylmethylthymidine (1.14 g, 3.03 mmol) and imidazole (985 mg, 15.15 mmol) in pyridine at was added a solution of t-butyldimethylchlorosilane (1.37 g, 9.09 mmol) in pyridine. The reaction mixture stood at 50° C. overnight, diluted with ethyl acetate (100 ml), washed with water (3×50 ml), concentrated. The residue was dissolved in ethanol (10 ml) and a mixture of ethylenediamine and ethanol (1:1, 20 ml) was added. the solution was heated at 50° C. for 2 days. Ethanol and ethylenediamine were evaporated under reduced pressure and the residue dissolved in chloroform (60 ml). The solution was washed with water (3×40 ml), dried (Na$_2$SO$_4$), and concentrated. The residue was purified by chromatography on silica (EtOAc-hexane, 1:1) to give 780 mg (52%) of 3', 5'-(bis-t-butyldimethylsilyl)-4'-C-hydroxymethylthymidine as a white solid.

Example 21

Preparation of 3',5'-(bis-t-butyldimethylsilyl)-4'-C-aminomethylthymidine

To a stirred solution of 3', 5'-(bis-t-butyldimethyl-silyl)-4'-C-hydroxymethylthymidine (500 mg, 1.0 mmol) and pyridine (0.4 ml) in anhydrous methylene chloride (5 ml) at 0° C. was added dropwise a mixture of trifluoromethane-sulfonic anhydride (564 mg, 332 μl, 2.0 mmol) and pyridine (0.4 ml) in methylene chloride (5 ml). The reaction mixture was stirred at 0° C. for 30 min. and 0.5 ml of 10% NaHCO$_3$ added at −10° C. The mixture was diluted with methylene chloride (20 ml), washed with cold 10% NaHCO3 (2×30 ml), dried (Na$_2$SO$_4$), concentrated, and dried under vacuum for 1 h. The crude was dissolved in dioxane (30 ml) and saturated with ammonia gas. The solution stood at room temperature overnight and then heated at 50° C. for 2 days. Excess ammonia and dioxane were evaporated and the residue purified by chromatography on silica (1% MeOH and 5% Et$_3$N in CHCl$_3$) to give 266 mg (53%) of 3',5'-(bis-t-butyl-dimethylsilyl)-4'-C-aminomethylthymidine as a white solid.

Example 22

Preparation of 3',5'-(bis-t-butyldimethylsilyl)-4'-C-trifluoroacetamidomethylthymidine A solution of 3',5'-(bis-t-butyldimethylsilyl)-4'-C-aminomethylthymidine (260 mg, 0.52 mmol) and ethyl thiotrifluoroacetate (635 mg, 0.52 ml, 4.0 mmol) in dioxane was stirred at room temperature for 5 h. Solvent was evaporated and the residue purified by chromatography on silica (5% methanol in chloroform) to give 220 mg (71%) of 3',5'-(bis-t-butyldimethylsilyl)- 4'-C-trifluoroacetamidomethylthymidine a white solid.

Example 23

Preparation of 4'-C-trifluoroacetamidomethylthymidine

A solution of 3',5'-(bis-t-butyldimethylsilyl)-4'-C-trifluoroacetamidomethylthymidine (215 mg, 0.36 mmol) and TBAF (1.0 M in THF, neutralized with acetic acid to pH=7.5, 0.72 ml) in THF (3 ml) stood at room temperature for 20 h. Solvent was evaporated and the residue purified by chromatography on silica (10% methanol in chloroform) to give chromatography on silica (10% methanol in chloroform) to give 118 mg (89%) of 4'-C-trifluoroacetamidomethylthymidine as a colorless solid.

Example 24

Preparation of 5'-O-(4,4'-domethoxytrityl)-4 -C-trifluoroacetamidomethylthymidine A solution of 4'-C-trifluoroacetamidomethylthymidine (110 mg, 0.3 mmol) and dimethoxytrityl chloride (152 mg, 0.45 mmol) in anhydrous pyridine (2 ml) stood at room temperature overnight. Pyridine was evaporated and the residue was purified by chromatography on silica (EtOAc-hexane, 2:1) to give 122 mg (61%) of 5'-O-(4,4'-dimethoxytrityl)-4'-C-trifluoroacetamidomethylthymidine as a foam.

Example 25

Preparation of 5'-O-(4,4'-domethoxytrityl)-4'-C-trifluoroacetamidomethyl-thym idine 3'-(2-cyanoethyl-N,N-diisopropylphoramidite)

To a stirred solution of 5'-O-(4,4'-dimethoxytrityl)-4'-C-trifluoro acetamidomethylthymidine (110 mg, 0.165 mmol) and diisopropylethylamine (129 mg, 174 μl, 1.0 mmol) in anhydrous methylene chloride (3 ml) at 0° C. under nitrogen was added dropwise a solution of 2-cyanoethyl-N,N-diisopropylchlorophosphoramidite (78 mg, 74 μl, 0.33 mmol) in methylene chloride (1 ml). The resulting solution was stirred at room temperature for 30 min., cooled to 0° C., and diluted with ethyl acetate (20 ml). The mixture was washed with 10% NaHCO$_3$ (3×15 ml), dried (Na$_2$SO$_4$), and concentrated. The residue was purified by chromatography on silica (Et$_3$N-EtOAc-hexane, 5:45:50) to give 137 mg (86%) of 5'-O-(4,4'-dimethoxytrityl)-4'-C-methoxymethylthymidine 3'-(2-cyanoehthyl-N,N-diisopropylphosphoramidite) as a foam.

Example 26

Preparation of 3', 5'-O-(bis-t-butyldimethylsilyl)-4'-C-azidomethylthymidine

To a stirred solution of 3', 5'-(bis-t-butyldimethylsilyl)-4'-C-hydroxymethylthymidine (0.95 g, 0.19 mmol) and pyridine (0.1 ml) in anhydrous methylene chloride (1 ml) at 0° C. was added dropwise a mixture of trifluoromethane-sulfonic anhydride (107 mg, 0.38 mmol, 63 μl) and pyridine (0.2 ml) in methylene chloride (2.5 ml). The reaction mixture was stirred at 0° C. for 30 min., cooled to −10° C., and 0.5 ml of 10% NaHCO$_3$ added. The mixture was diluted with cold methylene chloride (10 ml, washed with cold 10% NaHCO$_3$ (2×10 ml), dried (Na$_2$SO$_4$), concentrated, and dried under vacuum for 10 min. The crude was dissolved in anhydrous DMF (1 ml) and sodium azide (50 mg) added. The mixture was heated at 50° C. for 14 h, diluted with ethyl acetate (20 ml), washed with water (5×10 ml), dried (Na$_2$SO$_4$), and concentrated. The residue was purified by chromatography on silica (10% ethyl acetate in methylene chloride) to give 42 mg of 3', 5'-O-(bis-t-butyldimethylsily)-4'-C-azidomethylthymidine as a foam.

Example 27

Preparation of 4'-C-azidomethylthymidine

A solution of 3',5'-O-(bis-t-butyldimethylsily)-4'-C-azidomethylthymidine (25 mg) and TBAF (1.0 M in THF, 0.5 ml) in THF ( 1 ml) stood at room temperature for 30 min. solvent was evaporated and the residue purified by chromatography on silica (6% MeOH in CH$_2$Cl$_2$) to give 11 mg of 4'-C-azidomethylthyidine as a colorless solid.

Example 28

Preparation of 3'-O-t-butyldimethylsilyl-5'-deoxy-5'-methylidenethymidine

A suspension of sodium hydride (60% in mineral oil, 2.88 g, 72 mmol) in anhydrous DMSO (100 ml) after stirring at 65° C. for 1.5 h under nitrogen was changed to a clear solution, which was cooled to room temperature and transferred to a cold, stirred suspension of methyltriphenylphosphonium bromide (27.0 g, 75.6 mmol) in DMSO (20 ml) under nitrogen. The reaction mixture was stirred at room temperature for 45 min. and a solution of 3'-O-t-butyldimethylsilyl-5'-formylthymidine (8.50 g, 24 mmol) in DMSO (40 ml) added with cooling. The reaction mixture was stirred at room temperature for 2 h, diluted with ethyl acetate (2 L), washed with brine (5×800 ml), dried (Na$_2$SO$_4$), concentrated. The crude was purified by chromatography on silica (EtOAc-hexane, 30:70) to give 6.79 g (80.2%) of 3'-O-t-butyldimethylsilyl-5'-deoxy-5'-methylidene-thymidine as a colorless solid, m.p. 122° (recrystalization from ethyl acetate and hexane).

Example 29

Preparation of 3'-O-t-butyldimethylsilyl-5'-C,O-methylenethymidine

A solution of 3'-O-t-butyldimethylsilyl-5'-deoxy-5'-methylidenethymidine (6.26 g, 17.78 mmol) and m-chloroperoxybenzoic acid (4.61 g, 26.68 mmol) in methylene chloride (160 ml) was stirred at room temperature overnight, diluted with methylene chloride (200 ml), washed with 10% NaHCO$_3$ (2×240 ml) and then with brine (160 ml), dried (Na$_2$SO$_4$), and concentrated. The residue was chromatographed on silica (EtOAc-hexane, 1:2) to give intact starting material (2.25 g, 35.9%), 3'-O-t-butyldimethylsilyl-5'-(S)-C,O-methylene-thymidine (3.2 g, 76%), and 3'-O-t-butyldimethylsilyl-5'-(R)-C,O- methylenethymidine (0.365 g, 8%).

Example 30

Preparation of 3'-O-t-butyldimethylsilyl-5'-C-methoxymethylthymidine

A solution of 3'-O-t-butyldimethylsilyl-5'-(R)-C,O-methylenethymidine (1.84 g, 5 mmol) and anhydrous potassium carbonate (1.38 g, 10 mmol) in methanol was stirred at room temperature for 90 h. Ethyl acetate (70 ml) was added and the mixture neutralized with acetic acid to pH 7. Solvents were evaporated and the residue was dissolved in methylene chloride (30 ml). Precipitates were filtered and the solution concentrated- The residue was purified by chromatography on silica (EtOAc-hexane, 1:1) to give 310 mg of intact starting material and 578 mg of 3'-O-t-butyldimethylsilyl-5'-C-methoxy-methylthymidine as a colorless solid.

Example 31

Preparation of 3'-O-t-butyldimethylsilyl-5'-C-trifluoro acetamidomethyl thymidine A solution of 3'-O-t-butyldimethylsilyl-5'-(R)-C,O-methylenethymidine (0.84 g, 2.28 mmol) in methanol was mixed with an ammonia-saturated methanol solution (10 ml). The resulting solution stood at room temperature for 15 h and then excess ammonia and methanol evaporated. The dried residue was dissolved in dioxane (10 ml) and ethyl thiotrifluoroacetate (1.80 g, 11.4 mmol, 1.46 ml) added. The reaction mixture was stirred at room temperature for 6 h and then solvent evaporated. The residue was chromatographed on silica (EtOAc-hexane, 1:1) to give 895 mg (81.8%) of 3'-O-t-butyldimethylsilyl-5'-C- trifluoroacetamidomethylthymidine a colorless solid.

Example 32

Preparation of 3'-O-t-butyldimethylsilyl-5'-(S)-C-cyanomethylthymidine

A mixture of 3'-O-t-butyldimethylsilyl-5'-(R)-C,O-methylenethymidine (0.77 g, 2.09 mmol) and potassium cyanide (520 mg, 8.0 mmol) in DMF (10 ml) was stirred at room temperature for 40 h, diluted with ethyl acetate (100 ml), washed with brine (5×60 ml), dried (Na$_2$SO$_4$), and concentrated. The crude was purified by chromatography on silica (EtOAc-hexane, 1:1) to give 3'-O-t-butyldimethylsilyl-5'-(S)-C-cyanomethyl-thymidine (580 mg, 70%) as a white solid.

Example 33

Preparation of 3'-O-t-butyldimethylsilyl-5'-(S)-C-azidomethylthymidine

A mixture of 3'-O-t-butyldimethylsilyl-5'-(R)-C,O-methylenethymidine (368 mg, 1.0 mmol) and potassium cyanide (325 mg, 5.0 mmol) in DMF (3 ml) was heated at 50° C. for 16 h, diluted with ethyl acetate (60 ml), washed with brine (5×40 ml), dried (Na$_2$SO$_4$), and concentrated. The crude was purified by chromatography on silica (EtOAc-hexane, 1:1) to give 3'-O-t-butyldimethylsilyl-5'-(S)-C-cyanomethyl-thymidine (173 mg, 42%) as a white solid.

Example 34

Preparation of 3'-O-t-butvldimethylsilyl-5'-C-allylthymidines

To a suspension of anhydrous cuprous cyanide (7.57 g, 84.7 mmol) in anhydrous THF at −5° C. under argon was added dropwise allylmagnesium bromide (2.0 M in THF, 46.6 ml, 93.2 mmol). The slurry was stirred for 15 min. at −5° C. and a cold solution of 3'-O-t-butyldimethylsilyl-5'-formylthymidine (5.0 g, 14.12 mmol) in THF (200 ml) added dropwise. The reaction mixture was stirred at room temperature for 6 h, quenched by adding 10% NaHCO$_3$ (150 ml) at 0° C., and diluted with ethyl acetate (200 ml). The organic layer was washed with 10% NaHCO3 (2×150 ml), dried (NA2SO4), and concentrated to give 5.18 g of crude 3'-O-t-butyldimethylsilyl-5'-C-allylthymidines (containing two 5'-(R) and 5'-(S) isomers). The two isomers (ratio: about 1:1) were separated by chromatography on silica with 15% EtOAc in CHCl$_3$).

Example 35

Preparation of 3'-O-t-butyldimethylsilyl-5'-O- (4,4'-dimethoxytrityl)-5'-(S)-C-methoxymethylthymidines A mixture of 3'-O-t-butyldimethylsilyl-5'-C-methoxymethylthymidine (258 mg, 0.645 mmol), dimethoxytrityl chloride (1.09 g, 3.22 mmol), and silver trifluoromethanesulfonic anhydride (835 mg, 3.22 mmol) in anhydrous pyridine (3 ml) was heated at 50° C. for 18 h. Pyridine was evaporated and the residue was chromatographed on silica (EtOAc-hexane, 1:1) gave 372 mg (82%) of 3'-O-t-butyldimethylsilyl-5'-O-(4,4'-dimethoxytrityl)-5'-(S)-C-methoxymethylthymidine as a white solid.

Similarly, the following compounds were prepared:

3-O-t-butyldimethylsilyl-5'-O-(4,4'-dimethoxy-trityl)-5'-(S)-C-cyano methylthymidine was prepared from 3'-O-t-butyldimethylsilyl-5'-(S)-C-cyanomethylthymidine;

3'-O-t-butyldimethylsilyl-5'-O-(4,4'-dimethoxytrityl)-5'-(S)-C-azidomethylthymidine was prepared from 3'-O-t-butyldimethylsilyl-5'-(S)-C-azidomethylthymidine.

3'-O-t-butyldimethylsilyl-5'-O-(4,4'-dimethoxytrityl)-5'-(S)-C-allylthymidine was prepared from 3'-O-t-butyldimethylsilyl-5'-(S)-C-allylthymidine.

3'-O-t-butyldimethylsilyl-5'-O-(4,4'-dimethoxytrityl)-5'-(R)-C-allylthymidine was prepared from 3'-O-t-butyldimethylsilyl-5'-(R)-C-allylthymidine.

3'-O-t-butyldimethylsilyl-5'-O-(4,4'-dimethoxytrityl)-5'-(S)-C-trifluoroacetamidomethylthymidine was prepared from 3'-O-t-butyldimethylsilyl-5'-(S)C-trifluoroacetamidomethylthym idine.

Example 36

Preparation of 5'-O-(4,4'-dimethoxytrityl) -5'-(S)-C-methoxymethylthymidines A solution of 3'-O-t-butyldimethylsilyl-5'-O-(4,4'-dimethoxytrityl)- 5'-(S)-C-methoxymethylthymidine (825 mg, 1.17 mmol) and TBAF (1.0 M in THF, 3.6 ml, 3.6 mmol) in THF (15 ml) stood at room temperature for 2 h. THF was evaporated and the residue chromatographed on silica (EtOAc-hexane, 3:2) to give 551 mg (80%) of 5'-O-(4,4'-di-methoxytrityl)-5'-(S)-C-methoxymethylthymidines.

Similarly, the following compounds were prepared:
5'-O-(4,4'-dimethoxytrityl)-5'-(S)-C-cyanomethyl-thymidine was prepared from 3'-O-t-butyldimethylsilyl-5'-O-(4,4'-dimethoxytrityl)-5'-(S)-C-cyanomethylthymidine.

5'-O-(4,4'-dimethoxytrityl)-5'-(S)-C-azidomethyl-thymidine was prepared from 3'-O-t-butyldimethyl silyl-5'-O-(4,4'-dimethoxytrityl)-5'-(S)-C-azidomethylthymidine-5'-O-(4,4'-dimethoxytrityl)-5'-(S)-C-allylthymidine was prepared from 3'-O-t-butyldimethylsilyl-5'-O-(4,4'-dimethoxytrityl)-5'-(S)-C-allylthymidine. 5'-O-(4,4'-dimethoxytrityl)-5'-(R)-C-allylthymdine was prepared from 3'-O-t-butyldimethylsilyl-5'-O-(4,4'-dimethoxytrityl)-5'-(R)-C-allylthymidine.

5'-O-(4,4'-dimethoxytrityl)-5'-(S)-C-trifluoro-acetamidomethylthymidine was prepared from 3'-O-t-butyl-dimethylsilyl-5'-O-(4,4'-dimethoxytrityl)-5'-(S)-C-trifluoro-acetamidomethylthymidine.

Example 37

Preparation of 5'-O-(4,4'-dimethoxytrityl)-5'-(S)-C-methoxymethyl-thymidines 3'-(2-cyanoethyl-N,N-diisopropylphosphoramidite)

To a solution of 3'-O-t-butyldimethylsilyl-5'-O-(4,4'-dimethoxytrityl)-5'-(S)-C-methoxymethylthymidine (490 mg, 0.83 mmol), diisopropylethylamine (646 mg, 0.87 ml, 5.0 mmol) in anhydrous dichloromethane (5 ml) at 0° C. under nitrogen was added dropwise a solution of 2-cyanoethyl-N, N-diisopropylchlorophosphoramidite (592 mg, 2.5 mmol, 558 μl) in dichloromethane (1 ml). The solution was stirred at room temperature for 40 min., cooled to 0° C., diluted with dichloromethane (60 ml), washed with cold, 5% NaHCO₃ (3×40 ml), dried (Na₂SO₄), and concentrated. The residue was purified by chromatography on silica (Et₃N-EtOAc-hexane, 5:45:50) to give 584 mg (89%) 5'-O-(4,4'dimethoxytrityl)-5'-(S)-C-methoxymethylthymidines 3'- (2-cyanoethyl-N, N-diisopropyl-phosphoramidite) as a foam.

Similarly, the following compounds were prepared:
5'-O-(4,4'-dimethoxytrityl)-5'-(S)-C-cyanomethyl-thymidine 3'-(2-cyanoethyl-N, N-diisopropylphosphoramidite) was prepared from 5'-O-(4,4'-dimethoxytrityl)-5'-(S)-C-cyanomethylthymidine.

5'-O- (4,4'-dimethoxytrityl)-5'-(S)-C-azidomethyl-thymidine 3'-(2-cyanoethyl-N, N-diisopropylphosphoramidite) was prepared from 5'-O-(4,4'-dimethoxytrityl)-5'-(S)-C-azidomethylthymidine.

5'-O-(4,4'-dimethoxytrityl)-5'-(S)-C-allylthymidine 3'-(2-cyanoethyl-N, N-diisopropylphosphoramidite) was prepared from 5'-O-(4,4'-dimethoxytrityl)-5'-(S)-C-allylthymidine.

5'-O-(4,4'-dimethoxytrityl)-5'-(R)-C-allylthymidine 3'-(2-cyanoethyl-N, N-diisopropylphosphoramidite) was prepared from 5'-O-(4,4'-dimethoxytrityl)-5'-(R)-C-allylthymidine.

5'-O-(4,4'-dimethoxytrityl)-5'-(S)-C-trifluoroacetamido methylthymidine 3'-(2-cyanoethyl-N,N-diisopropyl-phosphoramidite) was prepared from 5'-O-(4,4'-dimethoxy-trityl)-5'-(S)-C-trifluoroacetamidomethylthymidine.

Example 38

Preparation of 1'-cyano-3'-t-butyldimethylsilyl-5'-(4, 4'-dimethoxytrityl)thymidine 1'-Cyano-5'-(4,4'-dimethoxytrityl)thymidine in anhydrous pyridine is added to a stirred solution of t-butyldimethylchlorosilane (1.5 equivalents) and imidazole (3.0 equivalents) in anhydrous pyridine at 0° C. The resulting reaction mixture is stirred at room temperature overnight. Pyridine is evaporated and the residue dissolved in ethyl acetate, washed with brine. The crude is directly used for the next reaction.

Example 39

Preparation of 3'-t-butyldimethylsilyl-5'-dimethoxytrityl-1'-formyl-5-methoxybenzyl thymidine 3'-t-butyldimethylsilyl-1'-cyano-5'-dimethoxy-trityl-5-(p-methoxybenzyl) thymidine (1.0 mmol) in THF is added to a stirred solution of lithium triethoxyaluminum hydride (2.0 mmol) in THF at −20° C. under nitrogen. The reaction mixture is stirred at 5–10° C. for 1 h, quenched with ammonium chloride aqueous solution. The mixture is extracted with ethyl acetate and the crude chromatographed on silica.

Example 40

Preparation of 1'-amido-3',5', 5-tris(methoxybenzyl) thymidine

1'-Amido-3', 5', 5-tris(methoxybenzyl)thymidine is added to a stirred aqueous solution of 30% hydrogen peroxide and sodium carbonate at 0° C. The reaction mixture is stirred at room temperature for 2 h, diluted with water, neutralized with dilute hydrochloric acid, extracted with dichloromethane. The crude is purified by chromatography.

Example 41

Preparation of 1'-amino-3', 5',5-tris(methoxybenzyl) thymidine.

The preparation procedure is similar as in described in the literature (Radhakrishna, A. S., Parham, M. E., Riggs, R. M., and Loudon, G. M. *J. Org. Chem.* 1979, 44, 1746). 1'-Cyano-3', 5',5-tris(methoxybenzyl)thymidine (1.0 mmol) in anhydrous THF is added to a stirred solution of I,I-bis (trifluoroacetoxy-iodobenzene (2.0 mmol) in THF at 0° C. The reaction mixture is stirred at room temperature for 5 h, diluted with dichloromethane, washed with 5% sodium carbonate and brine. The crude is purified by chromatography.

Example 42

Preparation of trimethyl-3', 5,5-tris(methoxybenzyl) thymidin-1'-yl ammonium bromide.

1'-Amino-3',5',5-tris(methoxybenzyl)thymidine is added to a stirred solution of methyl bromide (10 equivalents) in THF at 0° C. The reaction mixture is stirred at 50° C. overnight. The solvent is evaporated and the crude is purified by recrystallization.

Example 43

Preparation of 1'-bromo-3', 5',5-tris(methoxybenzyl) thymidine.

The procedure is similar as in the literature (Deady, L. W., Korytsky, O. L. *Tetrahedron Lett.* 1979, 451). Trimethyl-3', 5',5-tris(methoxybenzyl)-thymidin-1-yl ammonium bromide is heated at 150° C. under vacuum overnight. The resulting product is used directly for next reaction.

Example 44

Preparation of 1'-ethoxy-3', 5',5-tris (methoxybenzyl) thymidine.

1'-bromo-3', 5', 5-tris(methoxybenzyl)thymidine in ethanol is added to a stirred solution of sodium ethoxide in ethanol at −10° C. The resulting reaction mixture is stirred at room temperature fro 1 h, neutralized with dilute hydrochloric acid. Ethanol is evaporated and the remaining mixture extracted with ethyl acetate. The crude is purified by chromatography to give a mixture of α and β diasteriomers.

Similarly, the following compounds are prepared:
- 1'-(4-nitrobutoxy)-3',5', 5-tris(methoxybenzyl)thymidine from 1'-bromo-3',5',5-tris(methoxybenzyl)thymidine and 4-nitributanol-1.
- 1'-Ethylthio-3', 5', 5-tris(methoxybenzyl)thymidine from 1'-(4-nitrobutoxy)-3', 5', 5-tris(methoxybenzyl)thymidine from 1'-bromo-3', 5',5-tris(methoxybenzyl)thymidine and 4-nitributanol-1.
- 1'-Ethylthio-3', 5', 5-tris(methoxybenzyl)thymidine from 1'-bromo-3', 5', 5-tris(methoxybenzyl)thymidine and sodium thioethoxide.

Example 45

Preparation of 1'-amino-thymidine

A suspension of 1'-amino-3', 5', 5-tris(methoxybenzyl) thymidine and 10% palladium on charcoal in ethanol is shaken in a hydrogenation apparatus under hydrogen pressure of 50 psi for 24 h. The solid is filtered and the filtrate concentrated. The crude is purified by recrystallization.

Example 46

Preparation of the sugar-modified oligonucleotides

This example illustrates the use of Compound 55 (FIG. 8) for the synthesis of a random oligonucleotide having sequence:

5'-d(ATC TCT CCG CTT CCT* TT* C)-3'

In this sequence A, C, G, and T represent the unmodified deoxyribonucleoside and T* represents 5'-C-aminomethylthymidine. The oligonuceotide in this example was synthesized by ABI 394 DNA Synthesizer. All the nucleosides are incorporated by using phosphoramidite chemistry. Incorporation of dA, dC, dG, and T is carried out by using the standard DNA synthesis reagents and the standard procedure. Owing to the steric hindrance of branched substituent at C5' position of thymidine, incorporation of T* is carried out by using longer coupling time (5 minutes). After the synthesis the work-up of synthesized oligonucleotide follows the standard procedure. The crude oligonucleotide was purified by reverse phase C18 acetonitrile as mobile phase. 62.4 ODs of the purified oligonucleotide were obtained.

Similarly, the following random sugar-modified oligonucleotides have been synthesized: 5'-C-Branched sugar-modified oligonucleotides:

1. 1,5'-TTCCTGTCTGATGGCTTC-3'
2. 5'-XXCCTGTCTGATGGCTTC-3'
3. 5'-TTCCTGTCXGATGGCTTC-3'
4. 5'-ATCTCTCCGCTTCCTTTC-3'
5. 5'-ATCTCTCCGCTTCCTTXC-3'
6. 5'-ATCTCTCCGCTTCCTXXC-3'
7. 5'-ATCTCXCCGCTXCCTTTC-3'
8. 5'-ATCTCTCCGCTTCCTTYC-3'
9. 5'-ATCTCTCCGCTTCCTYYC-3'
10. 5'-ATCTCTCCGCTTCCYTYC-3'
11. 5'-AYCTCYCCGCTYCCTTYC-3'
12. 5'-ATCTCTCCGCTTCCTTZC-3'
13. 5'-ATCTCTCCGCTTCCTZZC-3'
14. 5'-ATCTCTCCGCTTCCZTZC-3'
15. 5'-ATCTCTCCGCTTCCTTVC-3'
16. 5'-ATCTCTCCGCTTCCTVVC-3'
17. 5'-ATCTCTCCGCTTCCVTVC-3'
18. 5'-ATCTCVCCGCVTCCTTTC-3'
19. 5'-AVCTCTCCGCTTCCTTTC-3'
20. 5'-ATCTCTCCGCTTCCTTWC-3'
21. 5'-ATCTCTCCGCTTCCTWWC-3'
22. 5'-ATCTCTCCGCTTCCWTWC-3'
23. 5'-ATCTCWCCGCWTCCTTTC-3'
24. 5'-AWCTCTCCGCTTCCTTTC-3'

X=5'-(S)-C-methoxymethylthymidine, Y=5'-(S)-C-aminomethylthymidine, Z=5'-(S)-C-cyanomethylthymidine, V=5'-(S)-C-allylthymidine, and W=5-(R)-C-allylthymidine.

4'-C-Branched sugar-modified oligonucleotides:

25. 5'-ATCTCTCCGCTTCCTTTC-3'
26. 5'-ATCTCTCCGCTTCCTTXC-3'
27. 5'-ATCTCTCCGCTTCCTXXC-3'
28. 5'-ATCTCTCCGCTTCCXTXC-3'
29. 5'-AXCTCTCCGCTTCCTTTC-3'
30. 5'-ATCTCXCCGCTXCCTTTC-3'
31. 5'-ATCTCTCCGCTTCCTTYC-3'
32. 5'-ATCTCTCCGCTTCCTYXC-3'
33. 5'-ATCTCTCCGCTTCCYTXC-3'
34. 5'-AYCTCTCCGCTTCCXTXC-3'
35. 5'-ATCTCYCCGCTYCCTTTC-3'

X=4'-C-methoxymethylthymidine. Y=4'-C-aminomethylthymidine.

3'-C-Branched sugar-modified oligonucleotides:

36. 5'-ATCTCTCCGCTTCCTTTC-3'
37. 5'-ATCTCTCCGCTTCCTTXC-3'
38. 5'-ATCTCTCCGCTTCCTXXC-3'
39. 5'-ATCTCTCCGCTTCCXTXC-3'
40. 5'-ATCTCTCCGCXTCCTTTC-3'
41. 5'-AXCTCTCCGCTTCCTTTC-3'
42. 5'-ATCTCTCCGCTTCCTTYC-3'
43. 5'-ATCTCTCCGCTTCCTYYC-3'
44. 5'-ATCTCTCCGCYTCCTTTC-3'

45. 5'-AYCTCTCCGCTTCCXTXC-3'
46. 5'-ATCTCYCGCTYCCTTTC-3'
47. 5'-ATCTCTCCGCTTCCTTZC-3'
48. 5'-ATCTCTCCGCTTCCTZZC-3'
49. 5'-ATCTCTCCGCTTCCZTZC-3'

X=3'-C-aminomethylthymidine, Y=3'-C-methylthymidine,
Z=3'-C-cyanomethylthymidine.

Incorporation by Reference

All patents, patents applications, and publications cited herein are hereby incorporated by reference.

Equivalents

The foregoing written specification is considered to be sufficient to enable one skilled in the art to practice the invention. Indeed, various modifications of the above-described invention which are obvious to those skilled in the field of organic chemistry or related fields are intended to be within the scope of the following claims.

What is claimed is:

1. A nucleoside having the structure:

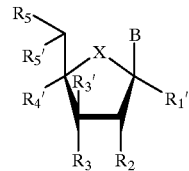

wherein:
   $R_2$ is selected from the group consisting of H, OH, alkoxy, aralkoxy and aryloxy;
   $R_3$ and $R_5$ are independently selected from the group consisting of OH, OCEPA and a hydroxyl blocking group;
   X is selected from the group consisting of O and $CH_2$;
   B is a nucleoside base;
   when X is $CH_2$,
      $R_1'$, $R_3'$, $R_4'$ and $R_5'$ are independently selected from the group consisting of H, CN, $N_3$, $NO_2$, $CF_3$, alky, substituted alkyl, aralkyl, substituted aralkyl, aryl, and substituted aryl, provided that $R_1'$, $R_3'$, $R_4'$ and $R_5'$ cannot all be H at the same time and $R_4'$ is not a label;
   when X is O,
      $R_4'$ and $R_5'$ are H, and
      $R_1'$ is selected from the group consisting of $N_3$, $NO_2$, $CF_3$, alky, substituted alkyl, aralkyl, substituted aralkyl, aryl, and substituted aryl, where the substituted portion of at least one of the substituted alkyl substituted aralkyl and substituted aryl is selected from the group consisting of $NO_2$, $N_3$, $CF_3$, SH, SR, COOH, COOR, $SO_3H$ $SO_3R$, F, Cl, Br, I, Ts, Ac, $CF_3CO$, acyl, where R is selected from lower alkyl aralkyl and aryl; and $R_3'$ is selected from the group consisting of CN, $N_3$, $NO_2$, $CF_3$, alkyl, substituted alkyl, aralkyl, substituted aralkyl, aryl, and substituted aryl, where the substituted portion of at least one of the substituted akl, substituted aralkyl and substituted aryl is selected from the group consisting of CN, $NO_2$, $N_3$, $CF_3$, $NH_2$, $NR_2$, OR, SH, SR, COOH, COOR, $SO_3R$, F, Cl, Br, I Ts, Ac, $CF_3CO$, acyl, where R is selected from lower alkyl, aralkyl and aryl; and wherein
any alkyl portion of $R_1'$, $R_3'$, $R_4'$ and $R_5'$ is C1 to C10, linear, branched, saturated or unsaturated.

2. The nucleoside of claim 1 wherein X is $CH_2$.
3. The nucleoside of claim 1 wherein X is O.

* * * * *